(12) United States Patent
Taguchi et al.

(10) Patent No.: US 9,418,451 B2
(45) Date of Patent: Aug. 16, 2016

(54) X-RAY CT APPARATUS, SUBSTANCE IDENTIFYING METHOD, AND IMAGE PROCESSING APPARATUS

(71) Applicant: Toshiba Medical Systems Corporation, Otawara-shi (JP)

(72) Inventors: Hiroki Taguchi, Otawara (JP); Masaharu Tsuyuki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 240 days.

(21) Appl. No.: 13/994,346

(22) PCT Filed: Sep. 24, 2012

(86) PCT No.: PCT/JP2012/074329
§ 371 (c)(1),
(2) Date: Jun. 14, 2013

(87) PCT Pub. No.: WO2013/047403
PCT Pub. Date: Apr. 4, 2013

(65) Prior Publication Data
US 2013/0287260 A1 Oct. 31, 2013

(30) Foreign Application Priority Data

Sep. 28, 2011 (JP) .................................. 2011-213047
Sep. 20, 2012 (JP) .................................. 2012-206419

(51) Int. Cl.
*G06T 11/00* (2006.01)
*G01N 23/04* (2006.01)
(Continued)

(52) U.S. Cl.
CPC ............ *G06T 11/003* (2013.01); *G01N 23/046* (2013.01); *G06T 11/005* (2013.01);
(Continued)

(58) Field of Classification Search
None
See application file for complete search history.

(56) References Cited

U.S. PATENT DOCUMENTS

| 2009/0262997 | A1 | 10/2009 | Zou et al. | |
| 2012/0093279 | A1* | 4/2012 | Akino | A61B 6/032 378/5 |
| 2014/0376686 | A1* | 12/2014 | Dreiseitel et al. | 378/5 |

FOREIGN PATENT DOCUMENTS

| CN | 1509686 A | 7/2004 |
| CN | 101028199 A | 9/2007 |

(Continued)

OTHER PUBLICATIONS

Johnson, T., et al., "Material differentiation by dual energy CT: initial experience," Eur Radiol, vol. 17, pp. 1510-1517, (2007).
(Continued)

*Primary Examiner* — Nirav G Patel
(74) *Attorney, Agent, or Firm* — Oblon, McClelland, Maier & Neustadt, L.L.P.

(57) ABSTRACT

An X-ray CT apparatus of an embodiment displays an image of the inside of an object based on projection data obtained by scanning the object, and comprises a generator, a converter, an image forming part and an identifier. The generator scans the object with each of X-rays of different energy levels and generates multiple projection data. The converter converts the multiple projection data into multiple new projection data corresponding to multiple reference substances. The image forming part reconstructs each of the multiple new projection data converted by the converter, thereby forming multiple reference substance images corresponding to the multiple reference substances. The identifier identifies a target substance based on a correlation of pixel values in the multiple reference substance images.

6 Claims, 19 Drawing Sheets

(51) Int. Cl.
*A61B 6/03* (2006.01)
*A61B 6/00* (2006.01)

(52) U.S. Cl.
CPC ............... *A61B 6/032* (2013.01); *A61B 6/482* (2013.01); *G01N 2223/206* (2013.01); *G01N 2223/419* (2013.01); *G01N 2223/6126* (2013.01); *G06T 2211/408* (2013.01)

(56) References Cited

FOREIGN PATENT DOCUMENTS

| JP | 2009 153829 | 7/2009 |
| JP | 2009 261942 | 11/2009 |
| JP | 2010 253138 | 11/2010 |

OTHER PUBLICATIONS

International Search Report Issued Nov. 27, 2012 in PCT/JP12/074329 Filed Sep. 24, 2012.
Combined Chinese Office Action and Search Report issued Dec. 29, 2014 in Patent Application No. 201280006252.4 (with English translation of categories of cited documents).

* cited by examiner

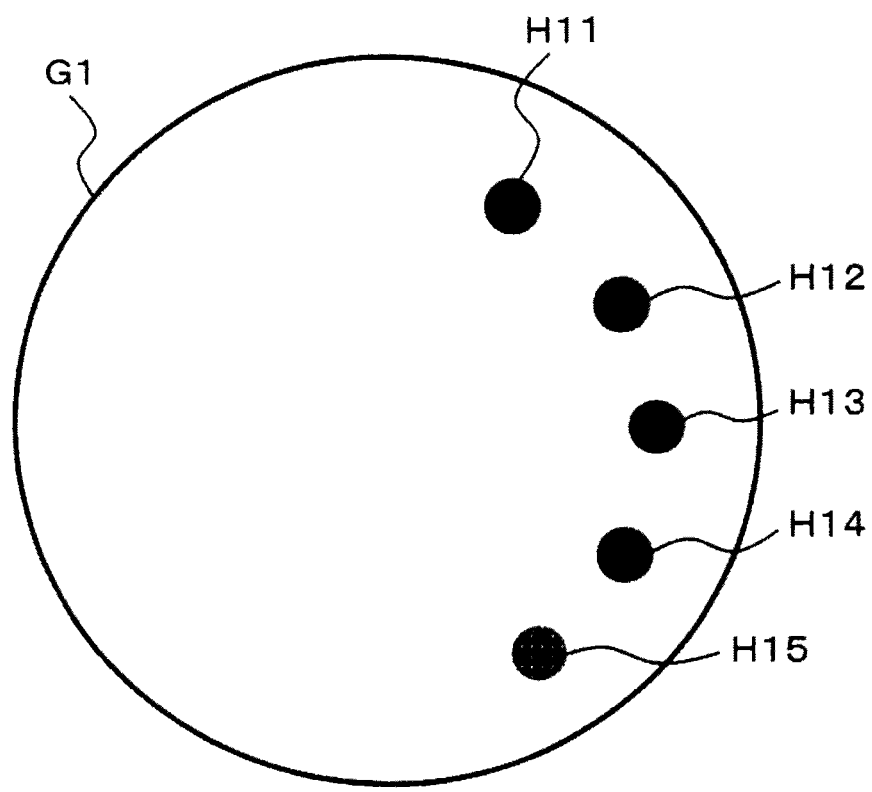

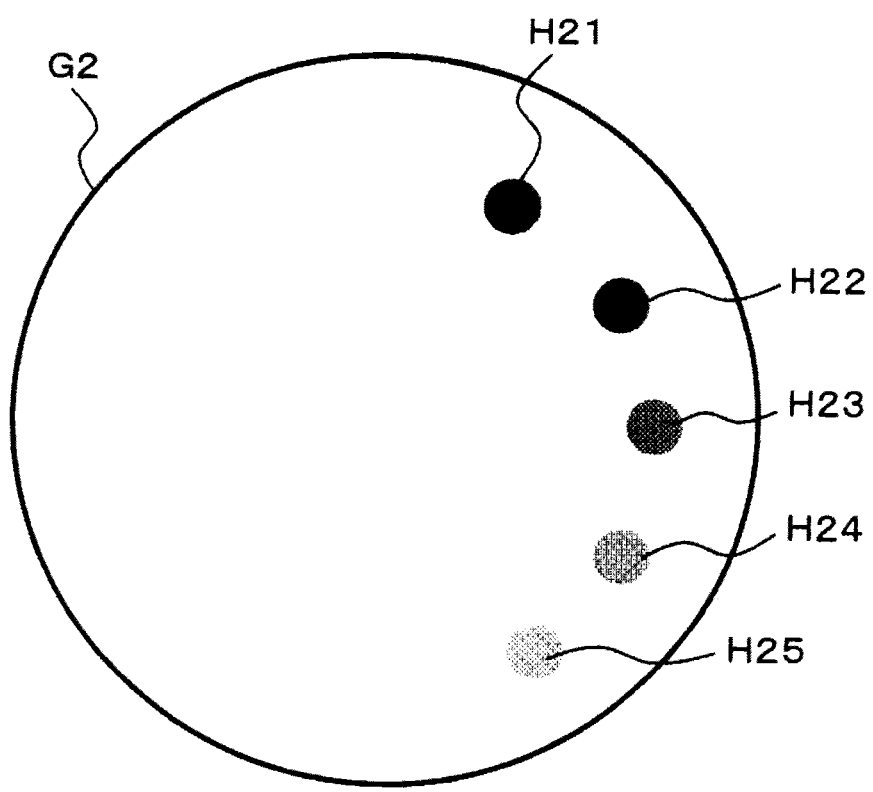

X-RAY CT APPARATUS, SUBSTANCE IDENTIFYING METHOD, AND IMAGE PROCESSING APPARATUS

TECHNICAL FIELD

Embodiments of the present invention relates to an X-ray CT apparatus, a substance identifying method, and an image processing apparatus.

BACKGROUND TECHNOLOGY

X-ray CT (Computed Tomography) is a technology wherein an image representing information of an object is formed by reconstructing projection data obtained by scanning the object with X-ray beams.

As an application of X-ray CT, there is technology that identifies a substance included in an object. In this technology, since it is difficult to determine a substance based on an image obtained by using X-ray beams of a single tube voltage, a method recently has attracted attention that involves taking individual scans with two X-ray beams of different energy levels by using two different tube voltages. This method is known as "dual energy CT."

Non-patent Document 1 describes technology wherein two images are formed by applying two different tube voltages, and a substance is identified by using ratios of the CT numbers of these images. It should be noted that any of the matters described in Non-patent Document 1 is made a reference as a part of the present specification.

Furthermore, Patent Document 1 describes technology wherein an image (reference substance image) is formed that expresses the distribution of various reference substances, through expressing the linear attenuation coefficient shown in each projection data obtained from the use of two different tube voltages as the linear combination of the linear attenuation coefficients of two reference substances (for example, water and bone). Furthermore, Patent Document 1 also describes methods for the formation of an effective atomic number image, a density image and a monochromatic X-ray image through combining these reference substance images. It should be noted that any of the matters described in Patent Document 1 is made a reference as a part of the present specification.

PRIOR ART DOCUMENTS

Patent Documents

[Patent Document 1] Japanese published unexamined application 2009-261942

Non-Patent Documents

[Non-patent Document 1] Johnson T R. et al., "Material differentiation by dual energy CT: initial experience", Eur Radiol (2007), 17, 1510-1517

SUMMARY OF THE INVENTION

Problem to be Solved by the Invention

Considering, however, that CT numbers are dependent on tube voltage and, as a result, a ratio of CT numbers is dependent on the combination of tube voltages, it has been difficult to precisely distinguish substances with similar CT number ratios using conventional dual energy CT technology.

Furthermore, although the use of conventional dual energy CT technology makes it possible to ascertain whether, based on reference substance images, the content of the reference substance is large or small, it is difficult to identify the type of the substance.

The problem to be solved by the present invention is to provide an X-ray CT apparatus, a substance identifying method, and an image processing apparatus that are capable of precisely identifying a substance contained in an object.

Means of Solving the Problem

An X-ray CT apparatus of an embodiment displays an image of the inside of an object based on projection data obtained by scanning the object, and comprises a generator, a converter, an image forming part and an identifier. The generator scans the object with each of X-rays of different energy levels and generates multiple projection data. The converter converts the multiple projection data into multiple new projection data corresponding to multiple reference substances. The image forming part reconstructs each of the multiple new projection data converted by the converter, thereby forming multiple reference substance images corresponding to the multiple reference substances. The identifier identifies a target substance based on a correlation of pixel values in the multiple reference substance images.

BRIEF DESCRIPTION OF THE DRAWINGS

FIG. 9B is a schematic diagram illustrating an example of an image displayed by the X-ray CT apparatus in the second embodiment.

FIG. 9C is a schematic diagram illustrating an example of an image displayed by the X-ray CT apparatus in the second embodiment.

MODE FOR CARRYING OUT THE INVENTION

The following is a description of an X-ray CT apparatus, a substance identifying method and an image processing apparatus in the embodiments, with reference to the diagrams. The following embodiments take an object body (patient) as an object; however, the object is not limited to this.

<First Embodiment>

[Configuration]

Figure 1:
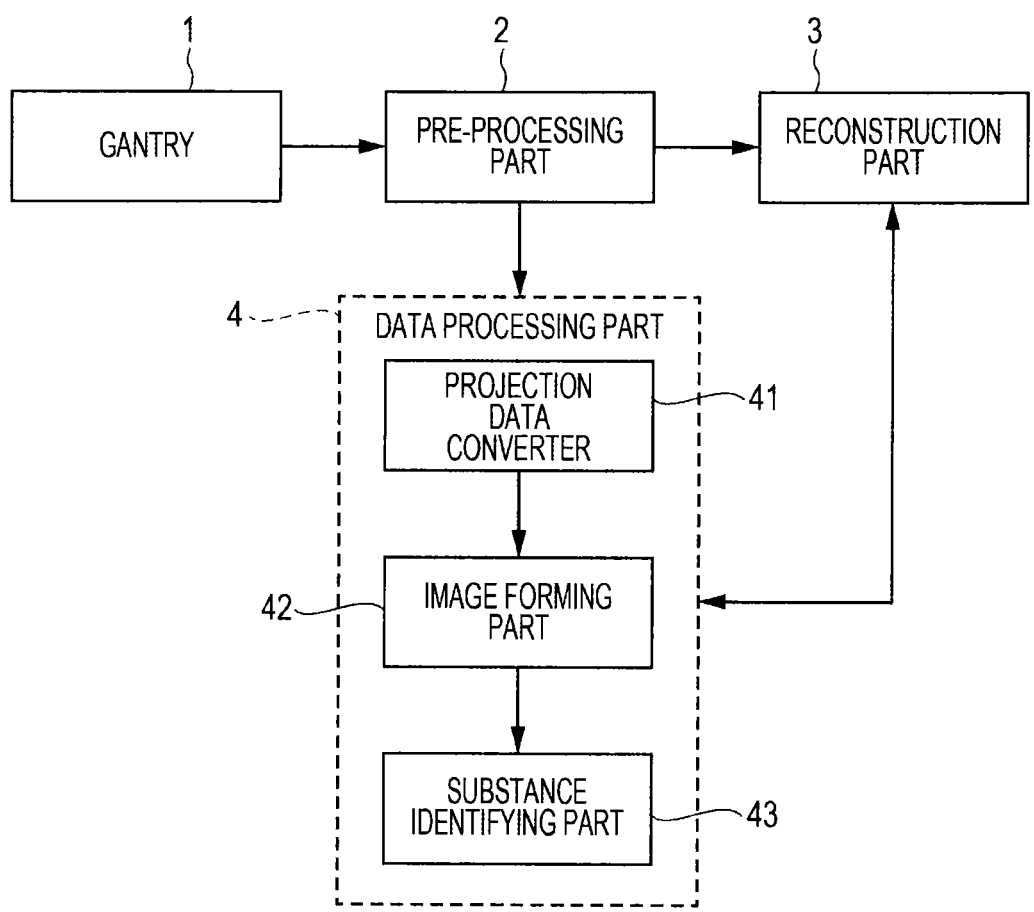
FIG. 1 is a block diagram illustrating an example of the outline of the configuration of the X-ray CT apparatus in the first embodiment.

The outline of the configuration of the X-ray CT apparatus in the embodiment is shown in FIG. 1. This X-ray CT apparatus comprises a gantry 1, a pre-processing part 2, a reconstruction part 3 and a data processing part 4. It should be noted that although not illustrated in the diagram, the X-ray CT apparatus in the embodiment also comprises a bed, a console, a high-voltage generation device, and other items similar to standard X-ray CT apparatus.

(Gantry 1)

The gantry 1 is used to scan the object body with X-rays. The gantry 1 is similar to standard gantries in that it is provided with an X-ray tube and an X-ray detector, which are positioned facing one another, a rotating mechanism that rotates these, a slip ring mechanism, a tilt mechanism, and a Data Acquisition System (DAS), etc. The gantry 1 scans the object body with X-rays while rotating the X-ray tube and the X-ray detector. The data detected by the X-ray detector is acquired by the DAS and transmitted to the pre-processing part 2.

The gantry 1 can, in particular, implement a method of scanning with X-ray beams of two difficult energy levels, that is, dual energy CT. The X-ray energy is dependent on the tube voltage applied to the X-ray tube by the high-voltage generation device. As the dual energy CT methods, there are the Slow-kV Switching method, the Dual Source method, and the Fast-kV Switching method. The Slow-kV Switching method is a method wherein after a scanning with a first tube voltage is carried out, a scanning with a second tube voltage is carried out (the two-rotation method). The Dual Source method is a method wherein a gantry with two X-ray tubes is used, and scanning is carried out by applying different tube voltages to each of these X-ray tubes (the two-tube method). The Fast-kV Switching method is a method wherein switching the tube voltage for each view while simultaneously rotating the X-ray tube and the X-ray detector (the high-speed switching method).

(Pre-Processing Part 2)

The pre-processing part 2 implements specified pre-processing (processing implemented prior to the image reconstruction) on the detected data transmitted from the gantry 1. This pre-processing may include calculation of logarithms of data, reference correction, water correction, beam hardening correction, body motion correction, etc. The data generated by the pre-processing part 2 is referred to as projection data. The projection data generated by the pre-processing part 2 is transmitted to the reconstruction part 3 and the data processing part 4. The gantry 1 and the pre-processing part 2 function as an example of the "generator."

(Reconstruction Part 3)

The reconstruction part 3 implements reconstruction processing on the projection data generated by the pre-processing part 2, thereby generating image data of the object body. The reconstruction processing involves arithmetic processing to inversely calculate the distribution of the X-ray absorption coefficient of the object body from the projection data. As this arithmetic processing, there are the 2D Fourier transform method, the convolution back-projection method, the fan beam convolution back-projection method, etc.

Furthermore, the reconstruction part 3 may be structured so as to generate image data by reconstructing projection data obtained by the data processing part 4. This process will be described below.

(Data Processing Part)

The data processing part 4 identifies substances included within the object body by implementing a specified data processing on the projection data generated by the pre-processing part 2.

The data processing part 4 is provided with a projection data converter 41, an image forming part 42, and a substance identifying part 43. It should be noted that the projection data converter 41 functions as an example of a "converter," the image forming part 42 as an example of an "image forming part," and the substance identifying part 43 as an example of an "identifier," respectively.

(Projection Data Converter 41)

The projection data converter 41 converts the first and second projection data obtained from the dual energy CT method into two projection data that correspond to two predetermined reference substances. An example of this process is that wherein the projection data converter 41 uses the method described in Patent Document 1 to express each of the first and second projection data as a linear combination including two predetermined reference values that correspond to the two reference substances and the aforementioned two projection data. In other words, the two coefficients in this linear combination become two target projection data. Further details of this processing example will be described below.

(Image Forming Part 42)

The image forming part 42 generates two reference substance images corresponding to the two reference substances, by reconstructing each of the two projection data obtained by the projection data converter 41. The reference substance images express the distribution of the linear attenuation coefficient in the object. The linear attenuation coefficient shows the extent of energy loss when X-ray passes through a substance of constant thickness. The information obtained from the reconstruction process is a linear combination image comprising the coefficients the two reference values and the two reference substance images. In other words, the two coefficients in the linear combination image become the two target reference substance images (reconstructed images).

This reconstruction processing is carried out using the same method as that used by the reconstruction part 3. It should be noted that the reconstruction part 3 may carry out this reconstruction process in place of the image forming part 42. In this case, the image forming part 42 is unnecessary. A more detailed example of the processing performed by the image forming part 42 or the reconstruction part 3 is given below.

The two reference values are used to express the linear attenuation coefficients of the projection data as a linear combination. The two reference values may be the linear attenuation coefficients of the two reference substances. Furthermore, the two reference values may be arbitrary values.

(Example of Processing)

The method described in Patent Document 1 is described here as an example of the processing described above. The first projection data (the one with a higher energy level) generated by the pre-processing part 2 is referred to as $g_H$, while the second projection data (the one with a lower energy level) is referred to as $g_L$. The projection data converter 41 generates two projection data $L_1$ and $L_2$, by applying the transformation shown in Equation (1) on these projection data $g_H$ and $g_L$.

[Equation 1]

$$\begin{pmatrix} L_1 \\ L_2 \end{pmatrix} = D^{-1} \begin{pmatrix} -L & -H \\ \mu_2 & -\mu_2 \\ -L & -H \\ -\mu_1 & \mu_1 \end{pmatrix} \begin{pmatrix} g_H \\ g_L \end{pmatrix} \quad (1)$$

Where:

D shows the determinant of the 2×2 matrix on the right hand side of the following Equation (2);

$<\mu>_{1, 2}^{H, L}$ shows the energy averaged linear attenuation coefficients described in Patent Document 1.

[Equation 2]

$$\begin{pmatrix} g_H \\ g_L \end{pmatrix} = \begin{pmatrix} -H & -H \\ \mu_1 & \mu_2 \\ -L & -L \\ \mu_1 & \mu_2 \end{pmatrix} \begin{pmatrix} L_1 \\ L_2 \end{pmatrix} \quad (2)$$

The image forming part 42 reconstructs the two projection data $L_1$ and $L_2$ shown in Equation (2), thereby forming two reference substance images ($c_1$ and $c_2$ in the following Equation (3)) corresponding to the two reference substances. The linear attenuation coefficient μ of arbitrary substance is, as shown in the following Equation (3), expressed as a linear combination (linear combination image) using the two reference values $\mu_1$ and $\mu_2$, and the two reference substance images $c_1$ and $c_2$.

[Equation 3]

$$\mu(E, x, y) = \mu_1(E)c_1(x, y) + \mu_2(E)c_2(x, y) \quad (3)$$

Where:

E shows the X-ray energy level;

$\mu_1$ (E) shows the linear attenuation coefficient (reference value) for the first reference substance at energy level E;

$\mu_2$ (E) shows the linear attenuation coefficient (reference value) for the second reference substance at energy level E;

$c_1$ (x, y) shows the abundance ratio of the first reference substance at the pixel positioned at a coordinate (x, y); and $c_2$ (x, y) is the abundance ratio of the second reference substance at the pixel positioned at a coordinate (x, y).

The reference substance images (abundance ratios) $c_1$ and $c_2$ are the coefficients obtained when the linear attenuation coefficient μ of arbitrary substance is expressed as a function of the linear attenuation coefficients $\mu_1$ and $\mu_2$ of the two reference substances, and are indicators of the extent to which the arbitrary substance is similar to each of the reference substances.

The following explanation is, in particular, an example in which the first reference substance is a contrast agent (iodine, density of 50 [mgI/ml]), while the second reference substance is water.

(Substance Identifying Part 43)

The substance identifying part 43 identifies the target substance based on the correlation of the two reference substance images formed by the image forming part 42. The target substance is the substance that is the target of type identification processing in the embodiment. When the processing example given above is applied, the substance identifying part 43, at first, for the specified target substance, determines coordinates corresponding to the two reference substance images $c_1$ and $c_2$ in a coordinate system predetermined based on the two reference values $\mu_1$ and $\mu_2$. Furthermore, the substance identifying part 43 identifies the target substance based on multiple coordinates in the aforementioned coordinates system, which are obtained in advance for specified multiple substances, and the coordinates corresponding to the two reference substance images $c_1$ and $c_2$, obtained by the previous processing.

Figure 2:
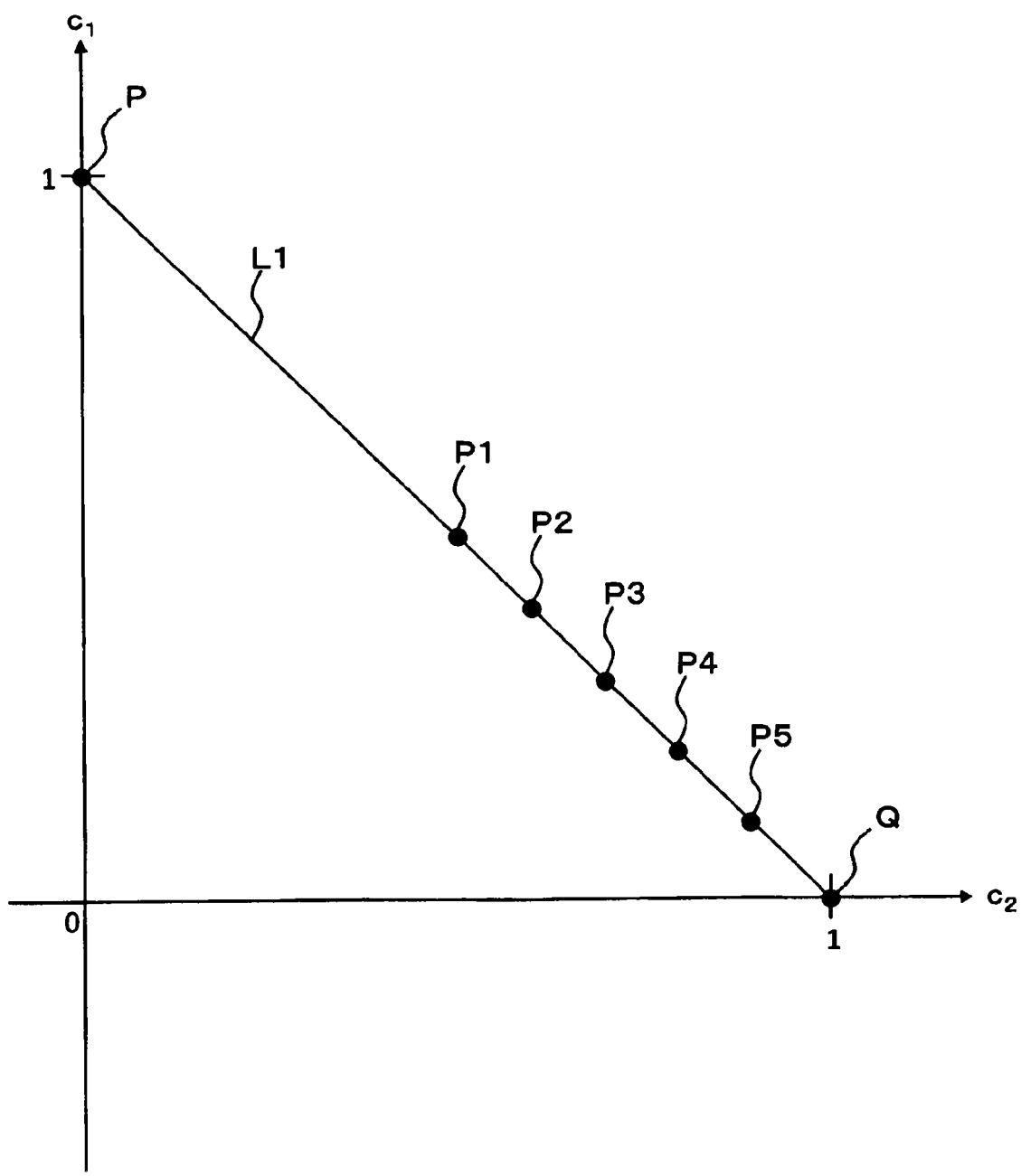
FIG. 2 is a graph for the purpose of describing the processes carried out by the X-ray CT apparatus in the first embodiment.

The aforementioned coordinate system can be set arbitrarily. As an example, it is possible to apply a two-dimensional coordinate system wherein the two abundance ratios $c_1$, $c_2$ are the bases as shown in FIG. 2. This coordinate system takes the abundance ratio $c_1$ of the contrast agent (the first reference substance) as the vertical axis, and the abundance ratio $c_2$ of water (the second reference substance) as the horizontal axis.

A coordinate in this coordinate system is denoted in order (a coordinate of the vertical axis, a coordinate of the horizontal axis). In other words, a coordinate in this coordinate system is written as ($c_1$, $c_2$). As a reference coordinate P (1, 0) on the vertical axis, that is, as a basis in the vertical direction, the vector is applied corresponding to a 100% abundance ratio $c_1$ of the contrast agent. Furthermore, As a reference coordinate Q (0, 1) on the horizontal axis, that is, as a basis in the horizontal direction, the vector is applied corresponding to a 100% abundance ratio $c_2$ of water.

The substance identifying part 43 treats the pair ($c_1$, $c_2$) of the reference substance images in the linear combination image obtained by the image forming part 42 as a coordinate in this coordinate system.

In this example, the coordinate system (bases) is provided such that the set of the reference substance images and the coordinate are expressed in the same way; however, this is not necessarily the case. For example, it is possible to use a coordinate system wherein the coordinate axes are extended or shortened by applying coefficients to $c_1$ and $c_2$. In this example, additionally, $c_1$ is allocated to the vertical axis and $c_2$ to the horizontal axis; however, these may be reversed. Furthermore, as an alternative to the orthogonal coordinate system such as this example, it is also possible to use other type of coordinate system such as an oblique coordinate system. In other words, the coordinate system in the embodiment is sufficient if it is capable of expressing the correlation of the two reference substance images in the linear combination image, wherein the specific aspect is arbitrary.

The aforementioned "multiple substances" provided for processing by the substance identifying part 43 are arbitrary. Moreover, the number of substances is also arbitrary. In the example shown in FIG. 2, the contrast agent and water corresponds to the multiple substances. In this example, the "multiple substances" and the substances used in the generation of the bases are the same; however, this is not necessarily the case. As an example of this, a case in which two substances, which are the contrast agent and water, are used as the two "reference substances," and five substances, which are a contrast agent, water, calcium carbonate, a lipid and uric acid, are used as the "multiple substances," is provided below.

The method for obtaining coordinates corresponding to the multiple substances is also arbitrary. Examples of this include the method of obtaining the coordinates by actually measuring the substances, and the method of calculating the coordinates by additionally considering the linear attenuation coefficients of other substances.

The former of the methods described above is implemented, for example, by: generating projection data by scanning the substance with X-rays; expressing the linear attenuation coefficient of each pixel based on this scanning as a linear combination; and determining coordinates corresponding to the set of the coefficient combinations thereof.

The following is a description of the latter of the methods described above. As the linear attenuation coefficient of each substance is already known, the following simultaneous equations (4a) and (4b) are obtained by substituting the linear attenuation coefficients corresponding to two different energy levels into Equation (3) above.

[Equation 4]

$$\mu(E_{Low}) = \mu_1(E_{Low})c_1 + \mu_2(E_{Low})c_2 \quad (4a)$$

$$\mu(E_{High}) = \mu_1(E_{High})c_1 + \mu_2(E_{High})c_2 \quad (4b)$$

Where:

$E_{Low}$ and $E_{High}$ shows two types of X-ray energy levels;

$\mu(E_{Low})$ shows the linear attenuation coefficient of this substance at the lower energy level $E_{Low}$, and $\mu(E_{High})$ shows the linear attenuation coefficient of this substance at the higher energy level $E_{High}$.

As the simultaneous equations (4a) and (4b) contain two unknowns $c_1$ and $c_2$, the pair of the coefficients $c_1$ and $c_2$ may be calculated by solving them. The required coordinates can be obtained based on the pair of the coefficients.

The substance identifying part 43 identifies the target substance, based on the multiple coordinates relating to the multiple substances obtained as above, and the coordinates specified by the substance identifying part 43 with regard to the target substance. In an example of this process, the substance identifying part 43 (1) obtains the region in the coordinate system based on the relevant multiple coordinates, and (2) identifies the target substance based on the position of the coordinate of the target substance with regard to this region. The following is a description of a case using a graph connecting the multiple coordinates as the region within the coordinate system. In such cases, unless specifically necessary, there is no need to actually display the region (graph, etc.) obtained in (1). In the following explanation, a displayed graph is utilized merely to facilitate understanding of the embodiment. The same applies to the regions within the coordinate systems described thereafter. It should be noted that a region within a coordinate system corresponds to a set of coordinates in this coordinate system, while a graph corresponds to a set of coordinates located in this region itself or the contour thereof.

The following is a description of the process used to obtain a graph as a region within the coordinate system. In the example shown in FIG. 2, the coordinate of the contrast agent and the coordinate of water are used as the aforementioned multiple coordinates. The substance identifying part 43 obtains line segment L1, which connects these coordinates, as the target graph.

In general, the formula of a line segment is obtained by calculating the formula of the straight line passing two coordinates based on the two coordinates (in other words, calculating the gradient and intercept), and extracting the part of this straight line of which the two coordinates represent the two ends. When three or more coordinates are considered and two or more line segments are being sought, the same calculation may be applied to arbitrary combination of two coordinates.

Here, the coordinates on the line segment L1 correspond to the iodine density of the contrast agent. For example, the coordinates P1, P2, P3, P4 and P5 on the line segment L1 correspond to iodine density of 25 [mgI/ml], 20 [mgI/ml], 15 [mgI/ml], 10 [mgI/ml] and 5 [mgI/ml], respectively. Furthermore, as described above, the coordinate P corresponds to 50 [mgI/ml], while the coordinate Q corresponds to 0 [mgI/ml] (merely water). In other words, the closer the coordinate gets to coordinate P along the line segment L1, the higher the density of iodine becomes, while the closer it gets to the coordinate Q, the lower the density of iodine becomes.

Using water as one of the multiple substances, as is the case here, allows the density of a substance to be expressed as a graph. When the five substances of a contrast agent, water, calcium carbonate, a lipid and uric acid are used, an example of the graphs is shown in FIG. 3.

Figure 3:
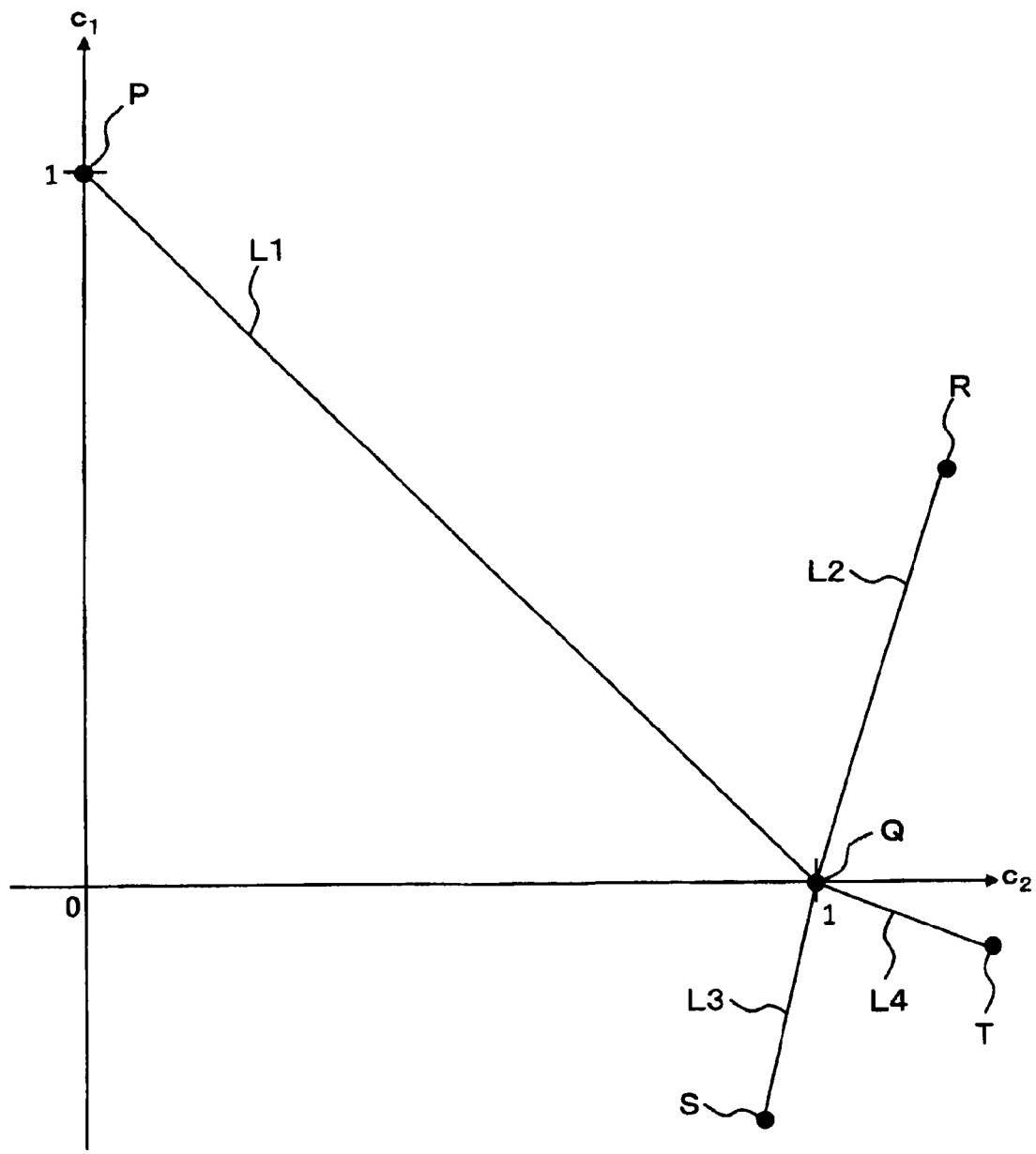
FIG. 3 is a graph for the purpose of describing the processes carried out by the X-ray CT apparatus in the first embodiment.

In FIG. 3, the coordinate P of the contrast agent, the coordinate Q of the water, the coordinate R of the calcium carbonate, the coordinate S of the lipid, and the coordinate T of the uric acid are shown. Furthermore, the line segment L1 connecting the coordinate P and the coordinate Q corresponds to the iodine density of the contrast agent, the line segment L2 connecting the coordinate R and the coordinate Q corresponds to the density of calcium carbonate, the line segment L3 connecting the coordinate S and the coordinate Q corresponds to the density of the lipid, and the line segment L4 connecting the coordinate T and the coordinate Q corresponds to the density of the uric acid. In each of the line segments L1 to L4, the closer the coordinate gets to the coordinate Q, the lower the density becomes, and the further away it gets from Q, the higher the density becomes.

Furthermore, as can be seen from FIG. 3, the four segments L1 to L4 only intersect with one another at the coordinate Q. This indicates that other than at the coordinate Q corresponding to the density 0 (pure water), segments L1 to L4 are separated from one another, that is, the coordinates corresponding to the four substances (contrast agent, calcium carbonate, lipid and uric acid) are separate from one another in this coordinate system. In other words, if locations of the line segments differ in this coordinate system, it can be concluded that the substances corresponding to them are different.

Using graphs of this type allows the substance identifying part 43 to identify the target substance, based on the positional relationship between the coordinate of the target substance determined by the substance identifying part 43 and the graphs.

Explaining the case, as an example, in which the line segments L1 to L4 shown in FIG. 3 are used as graphs, the substance identifying part 43 first determines whether or not the coordinate of the target substance is located on any of the line segments L1 to L4.

When the coordinate of the target substance is determined as being positioned on the line segment Li (where i=any of 1 to 4), the substance identifying part 43 identifies the target substance based on the position of this coordinate on the line segment Li. This identification includes not only the name of the target substance, but also its density (in other words, the component ratio of the target substance and water).

It should be noted that it is possible to identify only the name of the substance. In this case, it is sufficient simply to identify the line segment Li on which the coordinate of the target substance is located.

On the other hand, when it is determined that the coordinate of the target substance is not located on any of segments L1 to L4, the substance identifying part 43 yields the result that the target substance is not equivalent to the substances corresponding to the line segments L1 to L4.

When coordinates have been obtained for three or more reference substances, it is possible to form a polygon connecting these coordinates as a region within the coordinate system. The region defined by this polygon is equivalent to mixtures of these reference substances. These mixtures means substances defined as that the component ratio of each of the reference substances is between 0 to 100% with the sum of the component ratios of all reference substances equivalent to 100%. Thus, the mixtures may include substances that only contain one or two of the three or more reference substances. A substance that contains only one of the reference substances corresponds to one of the vertices of the polygon, while a substance that contains only two of the reference substances corresponds to one of the sides of the polygon.

Figure 4:
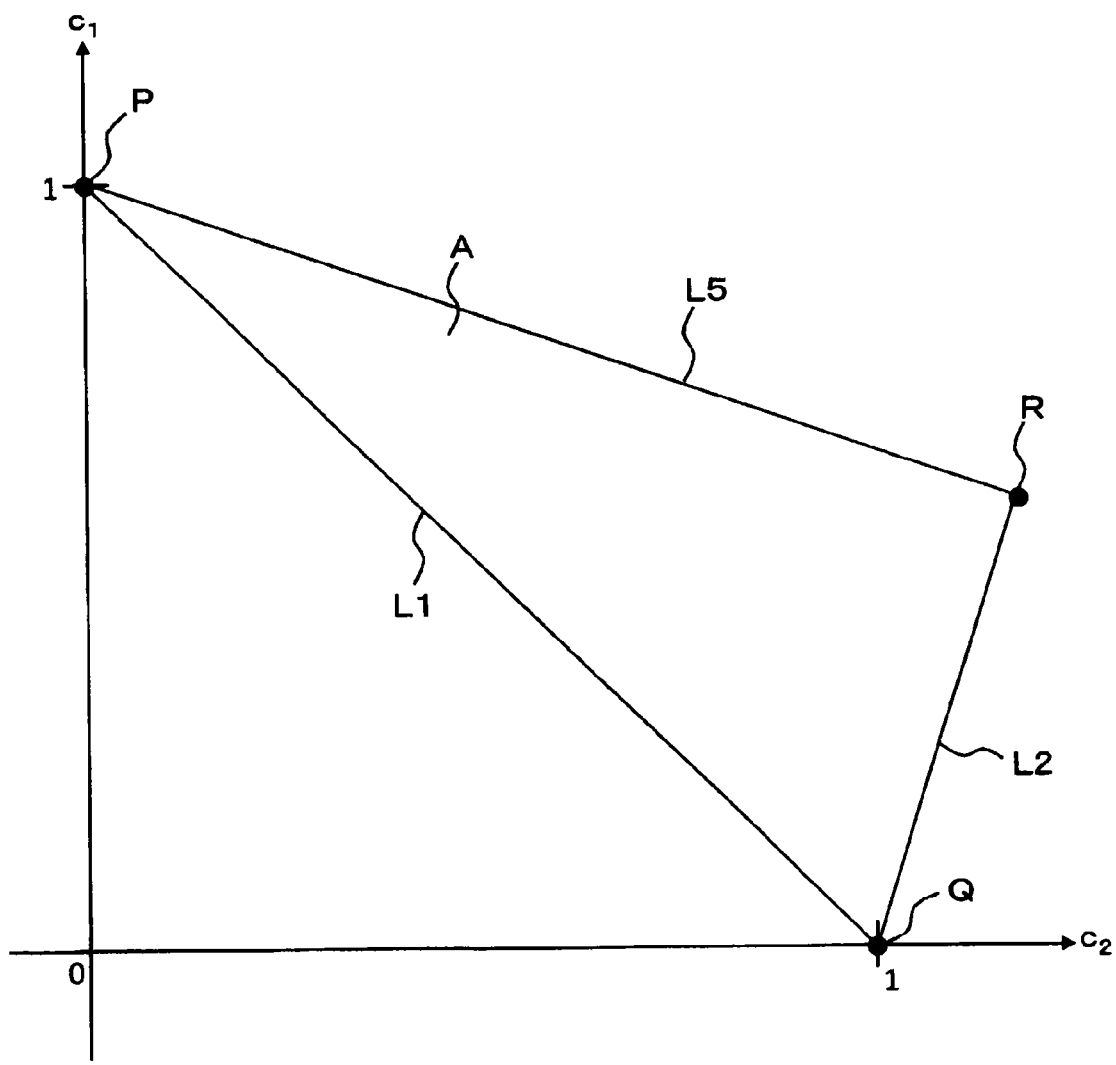
FIG. 4 is a graph for the purpose of describing the processes carried out by the X-ray CT apparatus in the first embodiment.

The following is a description of an example in which three or more reference substances are used, taking a contrast agent, water and calcium carbonate as three reference substances. In this case, as shown in FIG. 4, a polygon (triangle) A is obtained, with the coordinates P, Q and R corresponding to the contrast agent, water and calcium carbonate, at the vertices. The regions corresponding to the side PQ (line segment L1) and the side QR (line segment L2) of the polygon A indicate, as mentioned above, the density of contrast agent and the density of calcium carbonate, respectively. In addition, the region corresponding to the side PR (line segment L5) indicates the component ratio of the contrast agent and calcium carbonate in a substance that is a mixture of the contrast agent and calcium carbonate. On the side PR, the closer the coordinates get to the vertex P, the greater the component ratio of the contrast agent becomes, while the closer they get to the vertex R, the greater the component ratio of calcium carbonate becomes.

Furthermore, the region inside the polygon A, in other words, the region obtained by removing the line segments L1, L2 and L5 from the polygon A, corresponds to mixtures containing all three reference substances. With the coordinates in this internal region, similarly, the closer the coordinates get to the vertex P, the greater the component ratio of the contrast agent becomes, while the closer they get to the vertex R, the greater the component ratio of calcium carbonate becomes. Furthermore, the closer the coordinates get to the vertex Q, which corresponds to water, the lower the density of the mixture becomes.

The substance identifying part 43 determines whether or not the specified coordinate of the target substance is positioned on the polygon. If it is determined that this coordinate is positioned outside the polygon, the substance identifying part 43 determines that the target substance is not a mixture corresponding to this polygon.

On the other hand, if it is determined that this coordinate is positioned on the polygon, the substance identifying part 43 determines that the target substance is a relevant mixture. Furthermore, the substance identifying part 43 calculates the composition ratio of the three or more reference substances composing the target substance, based on the position of the coordinate of the target substance.

It should be noted that, in the example above, since measurement errors by the X-ray CT apparatus are not taken into consideration, it is assumed that the coordinate corresponding to each substance is uniquely determined. The measurement errors may be caused by mechanical differences (tolerance, etc.) or noises. The following is a description of processing in cases wherein the measurement errors are considered. It should be noted that if the measurement error is small enough that it can be allowed, it is sufficient to implement the processes described above.

The following is a description of one case in which measurement error is considered. Firstly, by performing repeated measurements for various substances, a coordinate distribution for each of the substances is obtained. This distribution information may, for example, be standard deviation information of noises mixed in the projection data obtained by the X-ray CT apparatus. This distribution information is stored in the substance identifying part 43.

Figure 5:
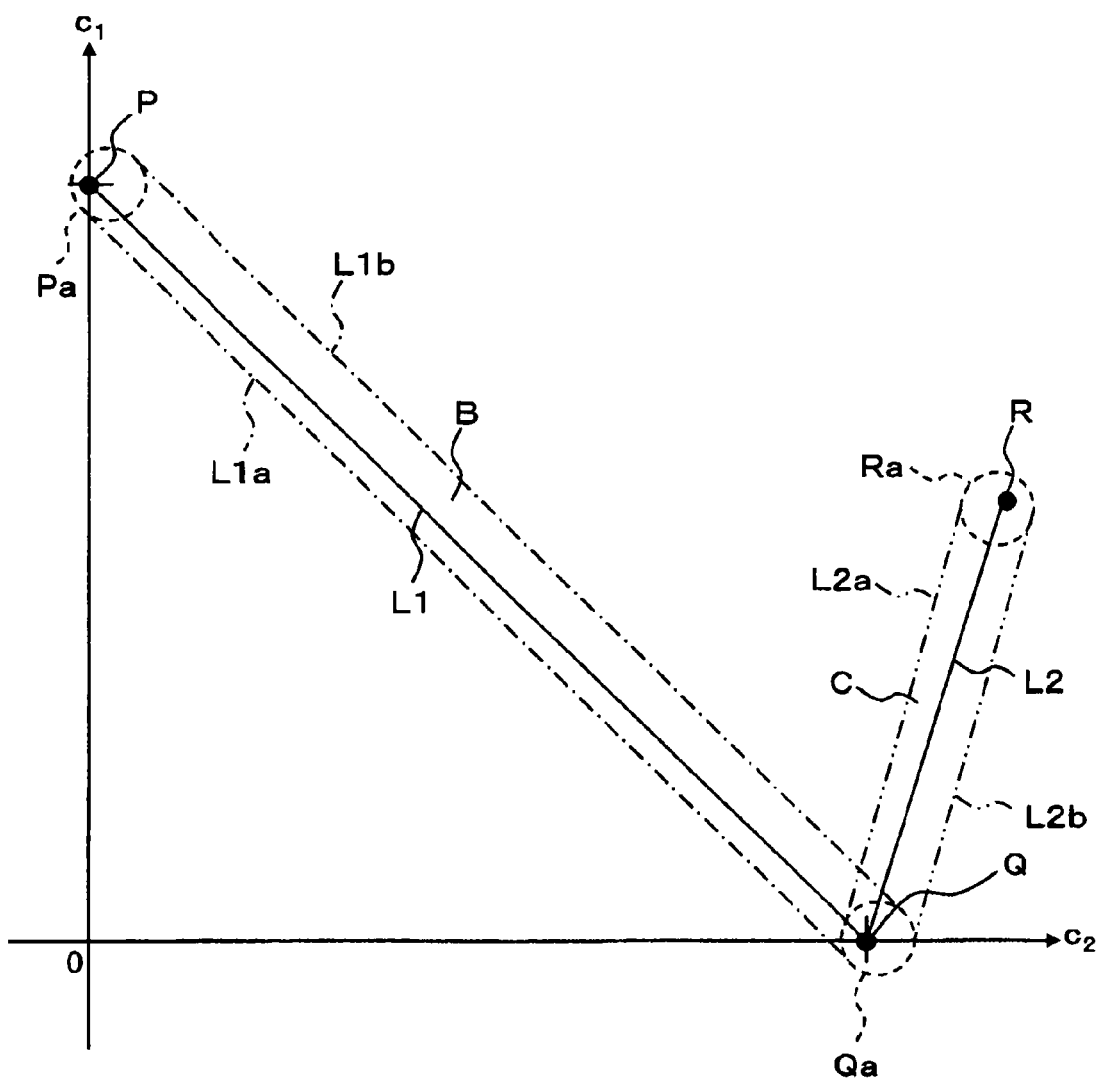
FIG. 5 is a graph for the purpose of describing the processes carried out by the X-ray CT apparatus in the first embodiment.

FIG. 5 shows an example of the distribution of coordinates for each of the contrast agent, water and calcium carbonate. The distribution range of the coordinates for the contrast agent is denoted by Pa, the distribution range of the coordinates for the water is denoted by Qa, and the distribution range of the coordinates for the calcium carbonate is denoted by Ra.

The substance identifying part 43 obtains a two-dimensional region including a graph corresponding to the relevant substance, based on the standard deviation information. The following is a description of an example of such processing. Firstly, the substance identifying part 43 obtains two line segments L1a and L1b, which join the distribution range Pa and the distribution range Qa. For example, line segments that are tangent to both distribution ranges Pa and Qa, and that do not intersect with one another, may be used as the line segments L1a and L1b. From this, a region B is obtained that is enclosed by the distribution ranges Pa and Qa and the line segments L1a and L1b. Similarly, a region C is obtained that is enclosed by the distribution ranges Ra and Qa and the line segments L2a and L2b.

The region B is used as the distribution range of the coordinates of the density of the contrast agent, in which measurement errors are reflected. Coordinates not on the line segment L1 in the region B are associated with density values based on the line segment L1. As an example of such association, it is possible to calculate the straight line intersecting the line segment L1 at each position on the line segment L1, and give the same density value to the coordinates that are positioned on this straight line. Density can be set in the same way for a region C showing the distribution range of calcium carbonate, in which measurement errors are reflected.

The substance identifying part 43 identifies the target substance based on positional relationship between the determined coordinates of the target substance and the regions B and C. If, for example, the coordinate of the target substance is located in region B, the substance identifying part 43 identifies the target substance as the contrast agent, and furthermore, identifies the density of the target substance based on this coordinate and the density defined for the coordinates in the region B.

[Operation]

Figure 6:
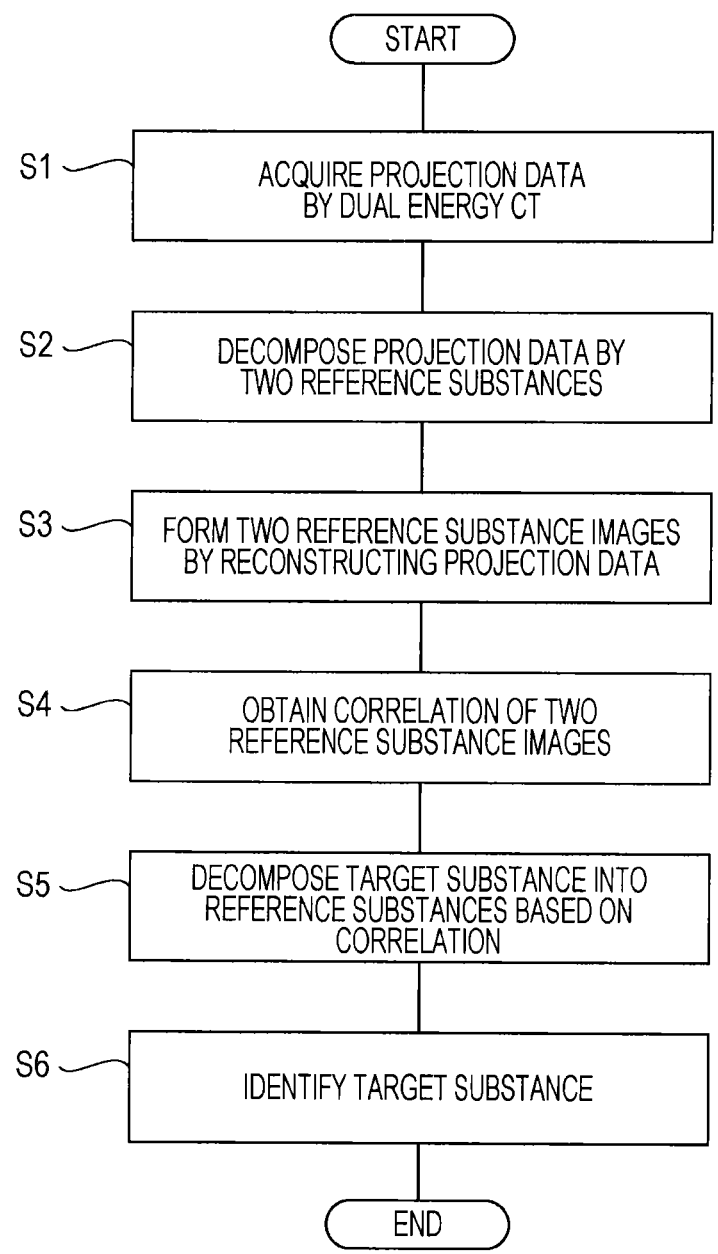
FIG. 6 is a flow chart illustrating an example of the operation of the X-ray CT apparatus in the first embodiment.

The following is a description of the operation of the X-ray CT apparatus in the embodiment. An example of the operation of the X-ray CT apparatus is shown in FIG. 6. Details of the operations of each part of the apparatus have been provided above, and therefore the following is merely a simple explanation.

(S1)

First, the gantry 1 implements an imaging by using dual energy CT. The pre-processing part 2 converts the data acquired by the gantry 1 into projection data. This allows the generation of the first and second projection data. The first and second projection data are sent to the data processing part 4.

(S2)

The projection data converter 41 expresses the linear attenuation coefficient of each pixel based on the projection data generated in step 1 as a linear combination of the linear attenuation coefficients of the two reference substances, thereby allowing decomposition of each projection data by the two reference substances. As a result of this step 2, the first and second projection data are converted into two projection data that correspond to the two reference substances.

(S3)

Furthermore, the image forming part 42 reconstructs the linear combination obtained in step 2 to form a linear combination image. This produces the two reference substance images.

(S4)

The substance identifying part 43 calculates the correlation between the two reference substance images obtained in step 3. In the example given above, for each pixel (x, y) of the two reference substance images, corresponding coordinate ($c_1(x, y)$, $c_2(x, y)$) in the specified two-dimensional coordinate system is obtained.

(S5)

The substance identifying part 43 decomposes the target substance into the two reference substances, based on the correlation obtained in step 4. In the example above, the target substance is decomposed into the contrast agent, water, etc.

(S6)

The substance identifying part 43 identifies the target substance based on the result of the decomposition in step 5. The results of this identification may be displayed, for example, on a display (not illustrated). Moreover, this identification result is stored in a storage device of the X-ray CT apparatus or a storage device on a network.

[Operation and Effect]

The following is a description of the operation and effect of the X-ray CT apparatus related to the embodiment.

This X-ray CT apparatus generates projection data using the gantry 1 and the pre-processing part 2. Specifically, by scanning the object using dual energy CT, that is, using each of X-rays with a first and a second different energy levels, a first and a second projection data are generated.

Furthermore, this X-ray CT apparatus comprises the projection data converter 41, the image forming part 42, and the substance identifying part 43. The projection data converter 41 converts the first and second projection data into two projection data (new projection data) that correspond to two predetermined reference substances. The image forming part 42 reconstructs the two projection data, thereby forming two reference substance images that correspond to the two reference substances. The substance identifying part 43 identifies the target substance based on the correlation of these two reference substance images.

The projection data converter 41 may be configured so as to, as the conversion process described above, express each of the first and second projection data as a linear combination including the two predetermined reference values corresponding to the two reference substances and the two projection data.

Furthermore, the image forming part 42 may be configured so as to reconstruct this linear combination, thereby forming a linear combination image including the two reference values and the two reference substance images.

Furthermore, the substance identifying part 43 may be configured so as to determine, for the target substance, coordinates corresponding to the two reference substance images in the coordinate system which is predetermined based on the two reference values, and to identify the target substance based on multiple coordinates in a coordinate system obtained in advance relating to multiple substances, and the determined coordinates.

It should be noted that, for each of the energy levels of the first and second X-rays, the two reference values may be the linear attenuation coefficients of the two pre-determined reference substances. Furthermore, the coordinate system may be a two-dimensional coordinate system spanned by two bases based on the linear attenuation coefficients of the two reference substances.

Furthermore, the substance identifying part 43 may be configured so as to identify the target substance based on the position of the coordinate of the target substance in relation to the region in the coordinate system based on the multiple coordinates.

Additionally, when the multiple substances include the first and second substances, the substance identifying part 43 may be configured to obtain the line segment that connects the coordinate of the first substance and the coordinate of the second substance in a coordinate system as a region within this coordinate system, and when the coordinate of the target substance is positioned on this line segment, to calculate the component ratio of the first substance and the second substance based on this position.

Furthermore, when the multiple substances include three or more reference substances, the substance identifying part 43 may be configured to obtain a polygon connecting the coordinates of the three or more substances in a coordinate system as a region within the above coordinate system, and if the coordinate of the target substance is positioned on this polygon, to calculate the component ratio of the three or more substances based on this position.

In the above example wherein the coordinates of three or more substances are considered, the region within the above coordinate system is not limited to polygons. In such cases, in general, the region within the above coordinate system may be a figure based on the coordinates of three or more substances, in other words, it may be an arbitrary figure that is formed in reference to these coordinates. For example, a figure that either passes through or encloses the coordinates of the three or more substances may be used as the region within the coordinate system as described above. In this example, there is no need for the outer periphery of the figure to be a straight line, nor is there any need for the coordinate of a substance to be on the outer periphery of the figure. If the coordinate of the target substance is positioned on the figure, the component ratio of the three or more substances can be calculated from this position.

Furthermore, if one of the multiple substances is water, the substance identifying part 43 may be configured to obtain the two line segments that connect each of the first and second coordinates determined for the first and second target substances, with the coordinates of water, as a region within a coordinate system, and to identify whether the first target substance and second target substance are the same or not, based on the positional relationship of these line segments.

Additionally, the substance identifying part 43 may be configured to store in advance standard deviation information related to noises mixed in projection data, to obtain a two-dimensional region including a region within a coordinate system based on this standard deviation information, and to identify the target substance based on the position of the coordinate of the target substance in relation to this two-dimensional region.

According to such X-ray CT apparatus, it is possible to express a characteristic of the target substance as a coordinate within a specified coordinate system, and to identify the target substance based on this coordinate and multiple coordinates corresponding to multiple substances. As a result, it is possible to differentiate with a high degree of precision even between substances with similar CT number ratios.

Furthermore, the application of a configuration that uses a region within the coordinate system described above allows the component ratios of the substances contained in the target substance to be calculated. In addition, by referring to a region within the coordinate system described above, it is possible to determine whether two or more target substances are the same or different.

Additionally, by applying a configuration that takes the impact of noises into consideration, it is possible to realize, with a greater degree of precision and accuracy, identification of substances, identification of composition ratios, and separation of target substances.

<Second Embodiment>

Figure 7:
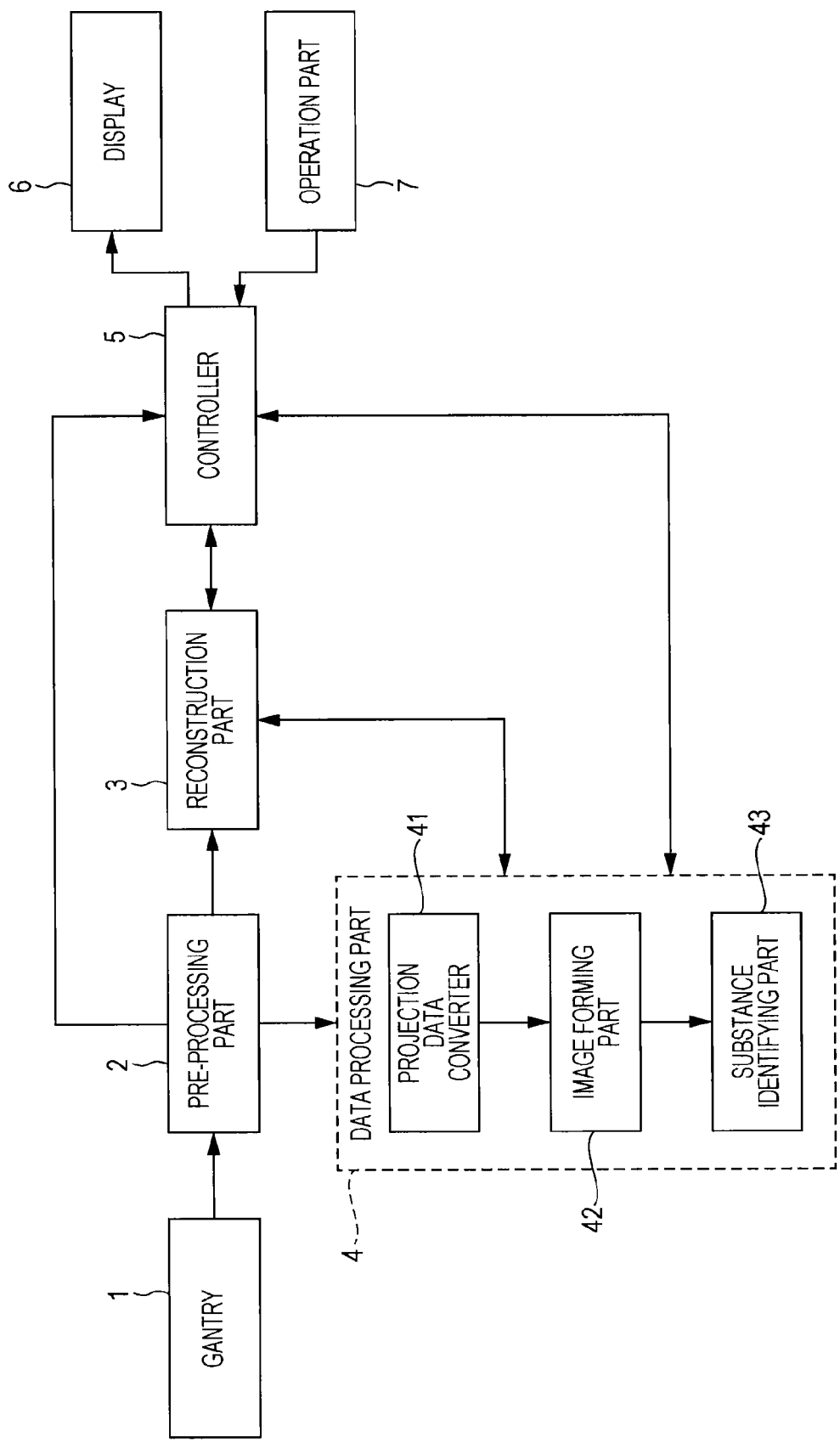
FIG. 7 is a block diagram illustrating an example of the outline of the configuration of the X-ray CT apparatus in the second embodiment.

The outline of the configuration of the X-ray CT apparatus in this embodiment is illustrated in FIG. 7. This X-ray CT apparatus comprises the configuration described in the first embodiment. This X-ray CT apparatus comprises a gantry 1, a pre-processing part 2, a reconstruction part 3 and a data processing part 4, a controller 5, a display 6 and an operation part 7. The data processing part 4 is provided with a projection data converter 41, an image forming part 42, and a substance identifying part 43. Components that are the same as those in the first embodiment have the same function as those in the first embodiment unless specifically mentioned.

It is assumed that one of reference substances is water. Additionally, the substance identifying part 43 obtains a line segment connecting the coordinate of the target substance and the coordinate of water, as described in the first embodiment 1 (see FIG. 2, etc.). This line segment shows the component ratio of the mixture of the target substance and water, that is the density of the target substance.

The data processing part 4 implements the processes in the first embodiment for each position within the imaging region of the object (object body etc.), thereby obtaining the distribution of the target substance in the imaging region. This distribution information is input to the reconstruction part 3. It should be noted that the distribution information includes information indicating the position of the presence of the target substance within the imaging region as well as information indicating its density.

The reconstruction part 3, upon receiving the distribution information and projection data, implements reconstruction processing to the target substance distribution region within the projection data, thereby forming a distribution image showing the distribution of the target substance (for example, density distribution). An example of this process is that in which the reconstruction part 3, based on the positions of presence of the target substance as indicated by the distribution information, identifies pixels corresponding to these positions of presence. The reconstruction part 3 then reconstructs images only for the identified pixels, based on the projection data. As other processes, the reconstruction part 3 implements ordinary reconstruction processing based on projection data, and then extracts, from among the images obtained thereby, only the pixels corresponding to the positions of presence. The reconstructed image obtained by these processes corresponds to the aforementioned distribution image.

The controller 5 receives designation of the position on the line segment showing the density of the target substance, and displays the distribution image on the display 6 in a mode according to the designated position. This process is described below.

This X-ray CT apparatus is provided with a user interface that is used for changing the density of the target substance. This user interface may be displayed on the display 6 based on software, or it may be hardware. Examples of hardware include dials and sliding bars. When software is used, it is possible, for example, to display images representing a dial or a sliding bar, and to operate them with the operation part 7.

Figure 8:
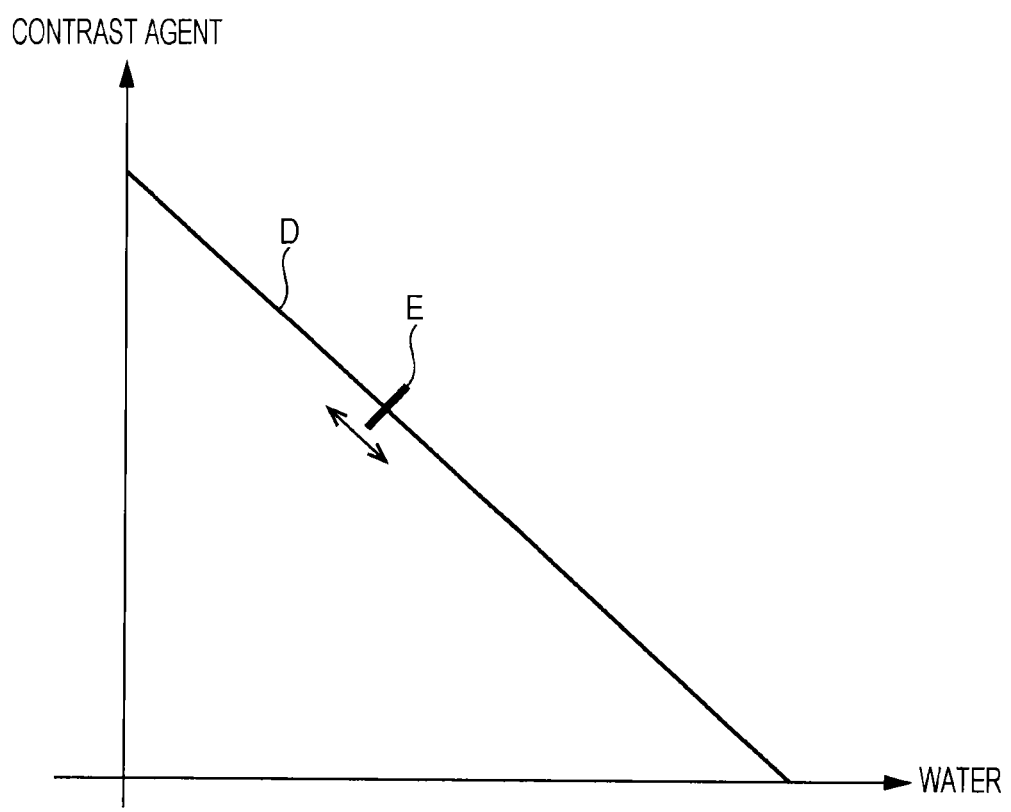
FIG. 8 is a schematic diagram illustrating an example of an image displayed by the X-ray CT apparatus in the second embodiment.

As a specific example using software, the controller 5 causes the display 6 to display the image shown in FIG. 8 based on the graph shown in FIG. 2. This image comprises a coordinate system as shown in FIG. 2, a line segment image D, and a slider E. The coordinate axes of the coordinate system have been annotated with the names of the substances, "CONTRAST AGENT" and "WATER." The line segment image D shows the line segment L1. The slider E can be moved on the line segment image D (see the arrows in both directions within the diagram). The slider E can be moved by, for example, drag operation using a mouse included in the operation part 7.

The user moves the slider E to the desired position, thereby designating the density of the contrast agent. More specifically, the line segment image D and the line segment L1 are associated in advance, and the position on the line segment L1 corresponding to the position of the slider E, that is, the density of the contrast agent is designated. The controller 5 changes the display mode of the distribution image in response to the designated density level. The process of changing the display mode may involve changing pixel values (luminance, color, etc.) or changing patterns, etc.

When multiple distribution images exist, it is possible to designate density for each of the distribution images. In such cases, the user may use a pointing device, for example, to designate the desired distribution image. The controller 5 displays the slider E in the position corresponding to the specified density for the designated distribution image. The user slides the slider E to the desired position. The controller 5 changes the display mode of this distribution image in response to the position of slider E after being moved.

As a process of changing density, it is also possible to use a method of inputting numerical values. In such cases, the controller 5 causes the display 6 to display an input region for inputting density information of the target substance. The user uses the operation part 7 (for example, a keyboard) to input the desired density value into the input region. The input region may be an object that allows the desired value to be selected from among multiple options of density, such as a pull-down menu.

A distribution image wherein density is increased from the initial value is sometimes called as an enhanced image. Furthermore, a distribution image wherein density is reduced from the initial value is sometimes called as a suppressed image.

Figure 9A:
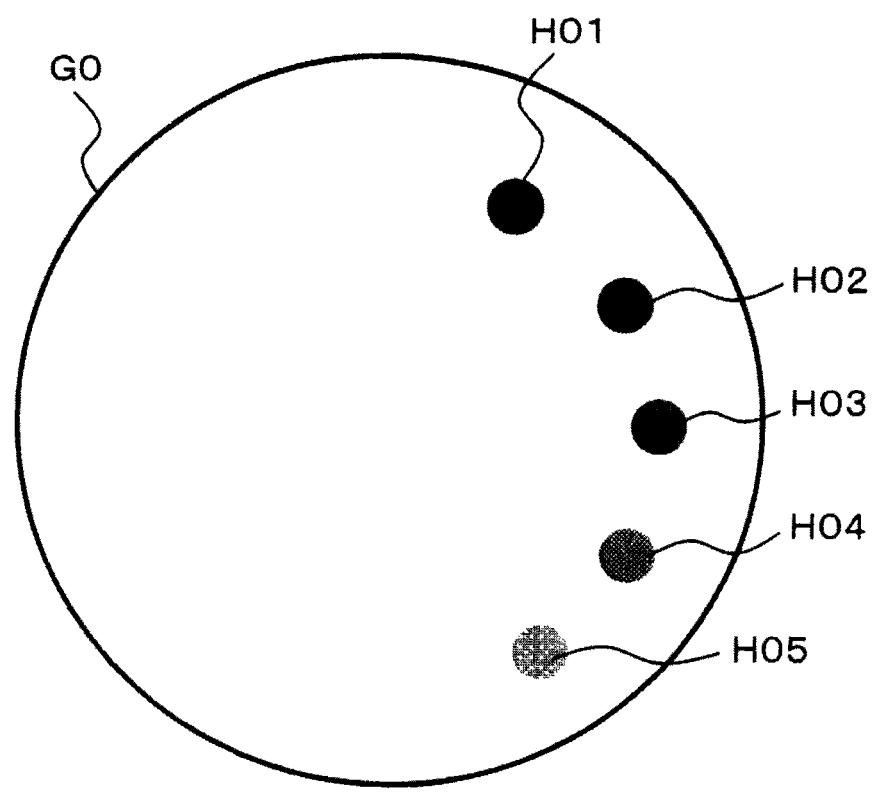
FIG. 9A is a schematic diagram illustrating an example of an image displayed by the X-ray CT apparatus in the second embodiment.

The following is a description of an example of an enhanced image and a suppressed image. FIG. 9A shows a distribution image (original image) G0 as a monochromatic X-ray image of 60 keV. It should be noted that in FIG. 9A (and same in the subsequent diagrams showing images) display luminance is reversed in comparison with the actual image. In other words, the higher the density of the target substance, the higher the display luminance in the actual image, however, in FIG. 9A, the higher the density, the lower the display luminance.

The monochromatic X-ray image is defined by the following Equation (5).

[Equation 5]

$$CTnumber(E, x, y) = 1000 \times \frac{\mu(E, x, y) - \mu_{water}(E, x, y)}{\mu_{water}(E, x, y)} \quad (5)$$

Where:
CT number shows CT number;
$\mu$ shows the linear attenuation coefficient of the target substance shown in Equation (5), and
$\mu_{water}$ shows the linear attenuation coefficient of water.

The distribution images H01, H02, H03, H04 and H05, which correspond to the contrast agent of various density values, are depicted in the original image G0. The distribution images H01, H02, H03, H04 and H05 correspond to density of 25 [mgI/ml], 20 [mgI/ml], 15 [mgI/ml], 10 [mgI/ml] and 5 [mgI/ml], respectively.

FIG. 9B shows the enhanced image G1 based on the original image G0. In the enhanced image G1, distribution images H11, H12, H13, H14 and H15, which respectively correspond to the distribution images H01, H02, H03, H04 and H05 in the original image G0, are depicted. Each distribution image H1$i$ (where i=1 to 5) indicates an increased state of density that is shown by the distribution image H0$i$.

FIG. 9C shows the suppressed image G2 based on the original image G0. In the suppressed image G2, distribution images H21, H22, H23, H24 and 1425, which respectively correspond to the distribution images H01, H02, H03, H04 and H05 in the original image G0, are depicted. Each distribution image H2$i$ (where i=1 to 5) indicates a reduced state of density that is shown in the distribution image H0$i$.

The following is a description of methods for generating the enhanced image G1 and the suppressed image G2. Firstly, the controller 5 identifies pixels corresponding to the coordinates that are positioned on the line segment L1 indicating the density of the contrast agent (see FIG. 2). Next, the controller 5, for each of the identified pixels, sets the abundance ratio $c_1$ of the contrast agent shown in Equation (3) at 1000, as well as sets the abundance ratio of water $c_2$ at 0, and then by substituting these into Equations (2a) and (2b), thereby generating the enhanced image G1. Furthermore, the controller 5 sets the abundance ratio $c_1$ of the contrast agent shown in Equation (3) at 0, as well as sets the abundance ratio of water $c_2$ at 1000, and then by substituting these into Equations (2a) and (2b), thereby generating the suppressed image G2. The controller 5 causes the display 6 to display the generated enhanced image G1 and suppressed image G2.

Next, an example of calculation method of density is explained. As noted above, a line segment within the coordinate system expresses a mixture of a substance and water, and positions on the line segment correspond to the density. For the case illustrated in FIG. 2, the line segment L1, which indicates the density of the contrast agent, is on a straight line with an inclination of −1 and an intercept of 1, allowing the density of the contrast agent to be calculated using the following formula.

[Equation 6]

$$\text{contrast\_agent\_density}[mgI/ml] = \frac{c_1}{c_1 + c_2} \times 50 [mgI/ml] \quad (6)$$

Figure 10:
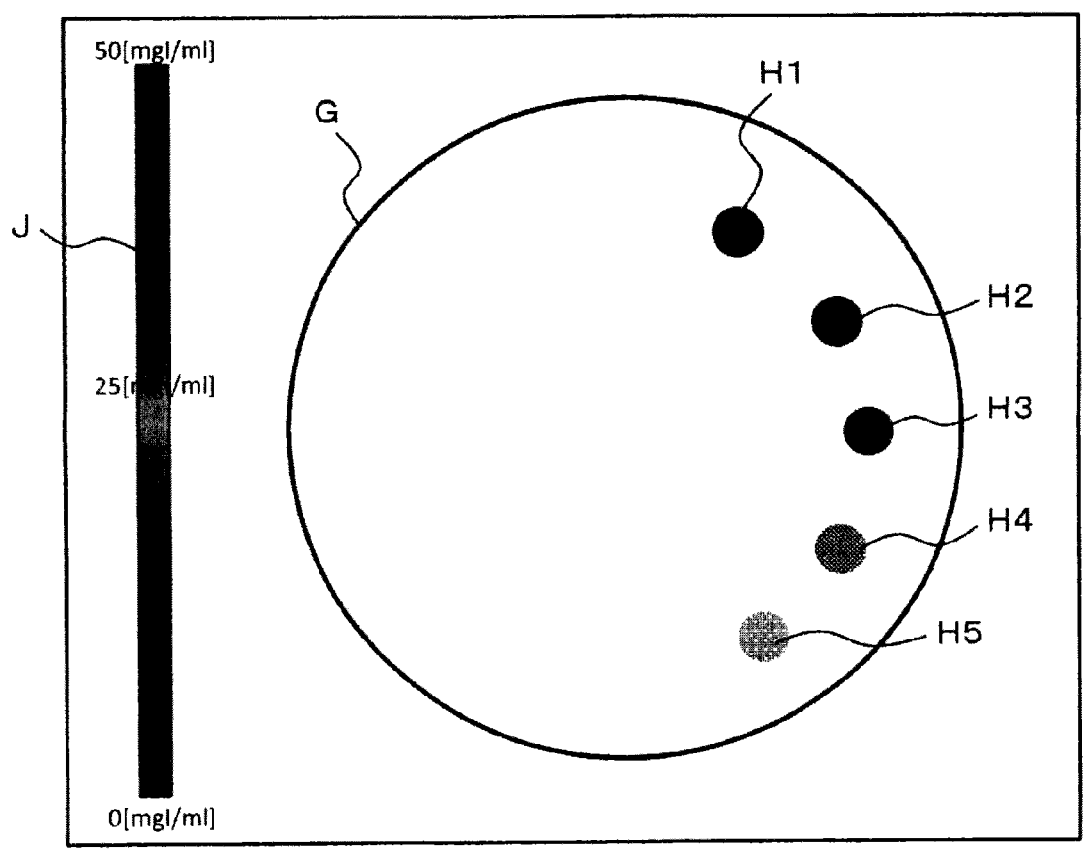
FIG. 10 is a schematic diagram illustrating an example of an image displayed by the X-ray CT apparatus in the second embodiment.

FIG. 10 schematically shows an example of a display mode in which the coefficients $c_1(x, y)$ and $c_2(x, y)$ corresponding to the coordinates that are positioned on the line segment L1 indicating the density of the contrast agent are extracted, and the density calculated using Equation (6) is color displayed. The five distribution images H1, H2, H3, H4 and H5 are depicted on the distribution image G. Each distribution image Hi (where i=1 to 5) is displayed in color according to its density. The relationship between density and display color is shown by the color bar J. It should be noted that when density of multiple substances are to be displayed in color, it is possible to configure to display distribution images with different colors according to substances.

The following is a description of the operation and effect of the X-ray CT apparatus in this embodiment.

In addition to the effects described in the first embodiment, the X-ray CT apparatus in this embodiment has the following effects. It should be noted that one of the substances is a solvent (for example, water). The substance identifying part 43 obtains the line segment connecting the coordinate of the target substance and the coordinate of the solvent. The reconstruction part 3 performs reconstruction processing on the distribution region of the target substance within the projection data, thereby forming a distribution image showing the distribution of the target substance. The controller 5 (display image generator) receives designation of the position on the line segment, forms a distribution image (display image) in an aspect according to the designated position, and displays it on the display 6.

Additionally, once the line segment image, which indicates the line segment, is displayed on the display 6 by the controller 5, and furthermore, the position on this line segment is designated using the operation part 7, the controller 5 may be configured so as to identify the position on the line segment corresponding to this designated position, and display a distribution image in the aspect according to this identified position.

Furthermore, once an input region for inputting density information of a substance may be displayed on the display 6, and further density information of a target substance is input into the input region using the operation part 7, the controller 5 (density calculator, display image generator) may be configured so as to identify the position on the line segment corresponding to this density information, and generate and display a distribution image in the aspect according to this identified position.

Moreover, the controller 5 may be configured so as to change the display color of the distribution image according to the designated position on the line segment. Furthermore, the controller 5 may be configured so as to change the display color of the distribution image depending on the kind of the target substance identified by the substance identifying part 43. In addition, the controller 5 may be configured so as to change the display color of the distribution image depending on both the kind of the target substance and the designated position on the line segment.

According to such X-ray CT apparatus, in addition to the effects of the apparatus described in the First Embodiment, it is possible to form and display an enhanced and/or a suppressed image. It is also possible to visualize the density of substances, facilitating an instinctive understanding of density.

In the example above, an explanation is provided of a case in which a line segment connecting the coordinate of the target substance and the coordinate of the solvent is obtained and a distribution image of the target substance is formed; however, it is also possible to apply substances other than solvents and perform similar processes. For example, it is possible to obtain the line segment connecting the coordinate of one of the aforementioned "multiple substances" and the coordinate of the target substance, and form a distribution image by implementing reconstruction processing to the distribution region of the target substance in the projection data. This distribution image shows the distribution of the target substance and the one substance. In other words, a single distribution image that expresses the distribution of two substances can be obtained.

<Third Embodiment>

According to the method described in the first embodiment, when the first line segment, which connects the coordinate of the first substance and the coordinate of water, and the second line segment, which connects the coordinate of the second substance and the coordinate of water, are near, it is difficult to distinguish between these substances. On the other hand, according to the method described in Non-Patent Document 1, it is difficult to distinguish between two substances when the CT number of the first substance and the CT number of the second substances are near.

This embodiment, therefore, provides a technology that combines these two methods to facilitate discrimination of substances. In addition, in this embodiment, processing is explained in which an effective atomic number image, a density image and a monochromatic X-ray image are formed by using the technology described in Patent Document 1.

Figure 11:
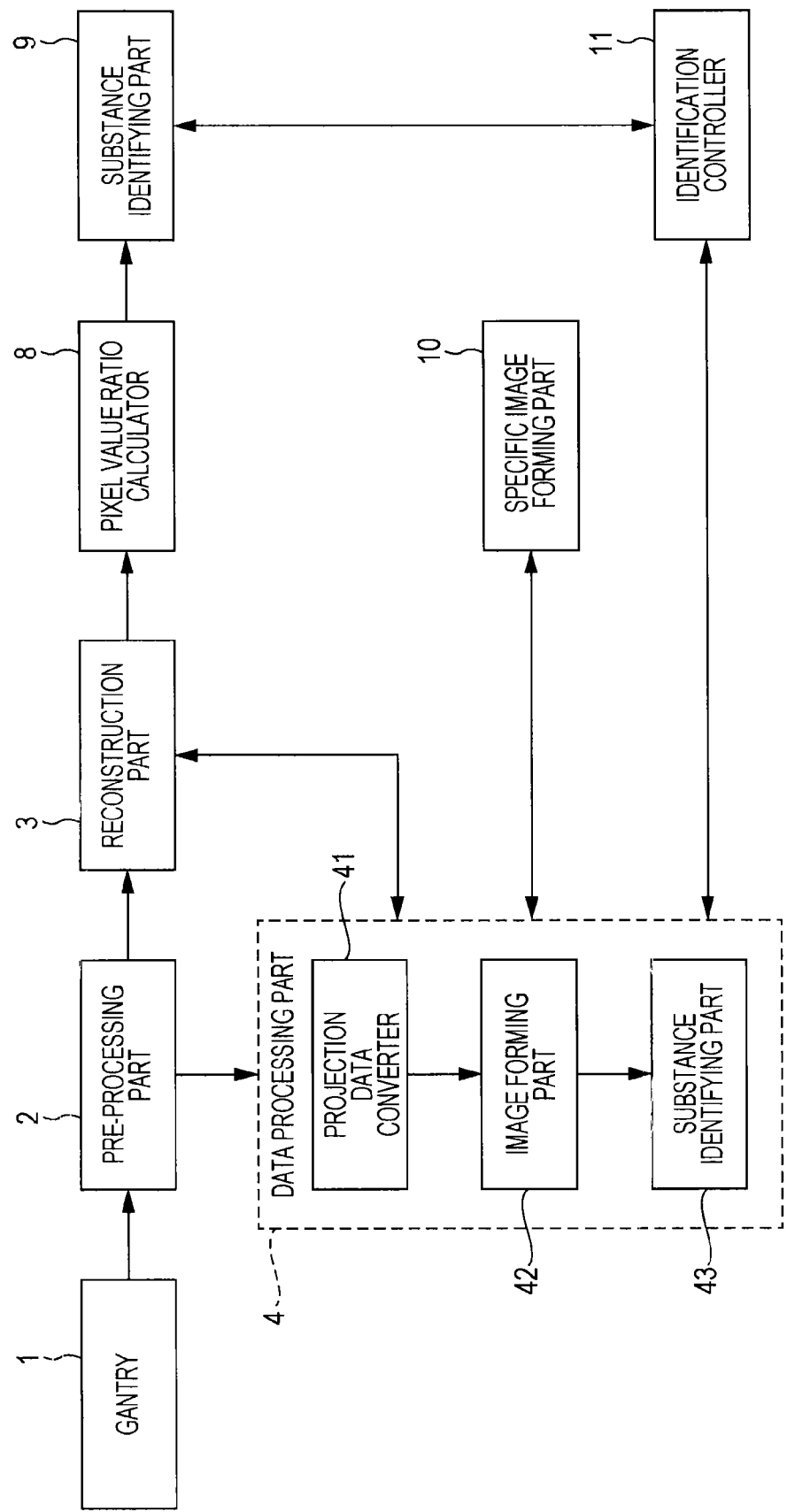
FIG. 11 is a block diagram illustrating an example of the outline of the configuration of the X-ray CT apparatus in the third embodiment.

The outline of the configuration of the X-ray CT apparatus in this embodiment is shown in FIG. 11. This X-ray CT apparatus comprises the configuration described in the first embodiment. Although not illustrated in the diagrams, this X-ray CT apparatus may also include the configuration described in the second embodiment.

This X-ray CT apparatus comprises a gantry 1, a preprocessing part 2, a reconstruction part 3 and a data processing part 4, a pixel value ratio calculator 8, a substance identifying part 9, a specific image forming part 10, and an identification controller 11. The data processing part 4 is provided with a projection data converter 41, an image forming part 42, and a substance identifying part 43. Each of the substance identifying part 9 and the identification controller 11 functions as an example of the "identifier."

Components that are the same as those in the first embodiment have the same functions as the first embodiment unless specifically mentioned. The substance identification process described in the first embodiment is carried out by the data processing part 4, while the substance identification process described in Non-Patent Document 1 is carried out by the pixel value ratio calculator 8 and the substance identifying part 9.

The reconstruction part 3 implements reconstruction processing on each of the first and second projection data obtained from the dual energy CT, forming the first and second images.

As described in Non-Patent Document 1, the pixel value ratio calculator 8 calculates the ratio of the pixel values (CT numbers) in the first and second images. This process involves establishment of an association of pixels between the first and second images, and calculation of the ratio of the CT numbers of the two pixels that have been associated.

The substance identifying part 9 identifies the target substance based on the CT number ratio calculated by the pixel value ratio calculator 8 using the method described in Non-Patent Document 1.

Figure 12:
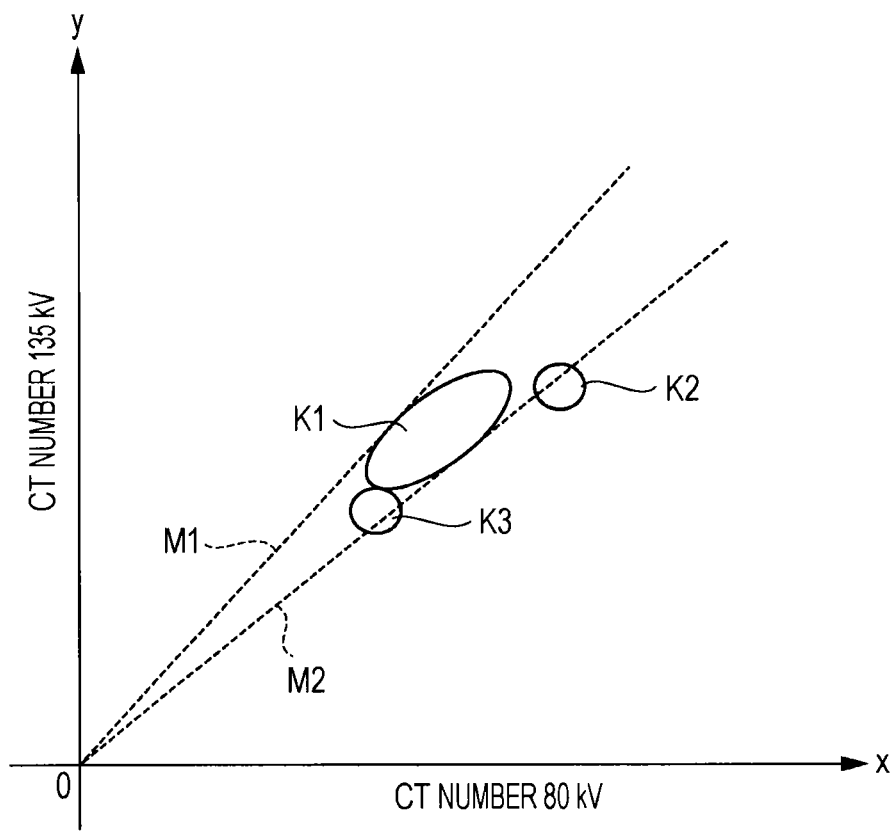
FIG. 12 is a schematic diagram for the purpose of describing the processes carried out by the X-ray CT apparatus in the third embodiment.

The following is a description of a specific example in which uric acid is identified in a situation wherein uric acid, cartilage and soft tissue exist. FIG. 12 shows an example of the distribution of the CT number ratio obtained for these substances. In this example, imaging is carried out using dual energy CT at tube voltages of 80 kV and 135 kV. In FIG. 12, the CT numbers at the tube voltage of 80 kV are shown on the x axis, while the CT numbers at the tube voltage of 135 kV are shown on the y axis. Thus, the slope of the straight line passing through both the origin and the arbitrary coordinate corresponds to the CT number ratio.

The distribution regions K1, K2 and K3 show the distributions of uric acid, cartilage and soft tissue, respectively. As can be seen from the positional relationship of the distribution regions K1, K2 and K3, the CT number ratios of uric acid and cartilage are different and it is possible to distinguish them from one another; however, since the CT number ratios of uric acid and soft tissue are near, it is difficult to distinguish them. The straight lines M1 and M2 show the maximum and minimum CT number ratios for uric acid, respectively.

Figure 13:
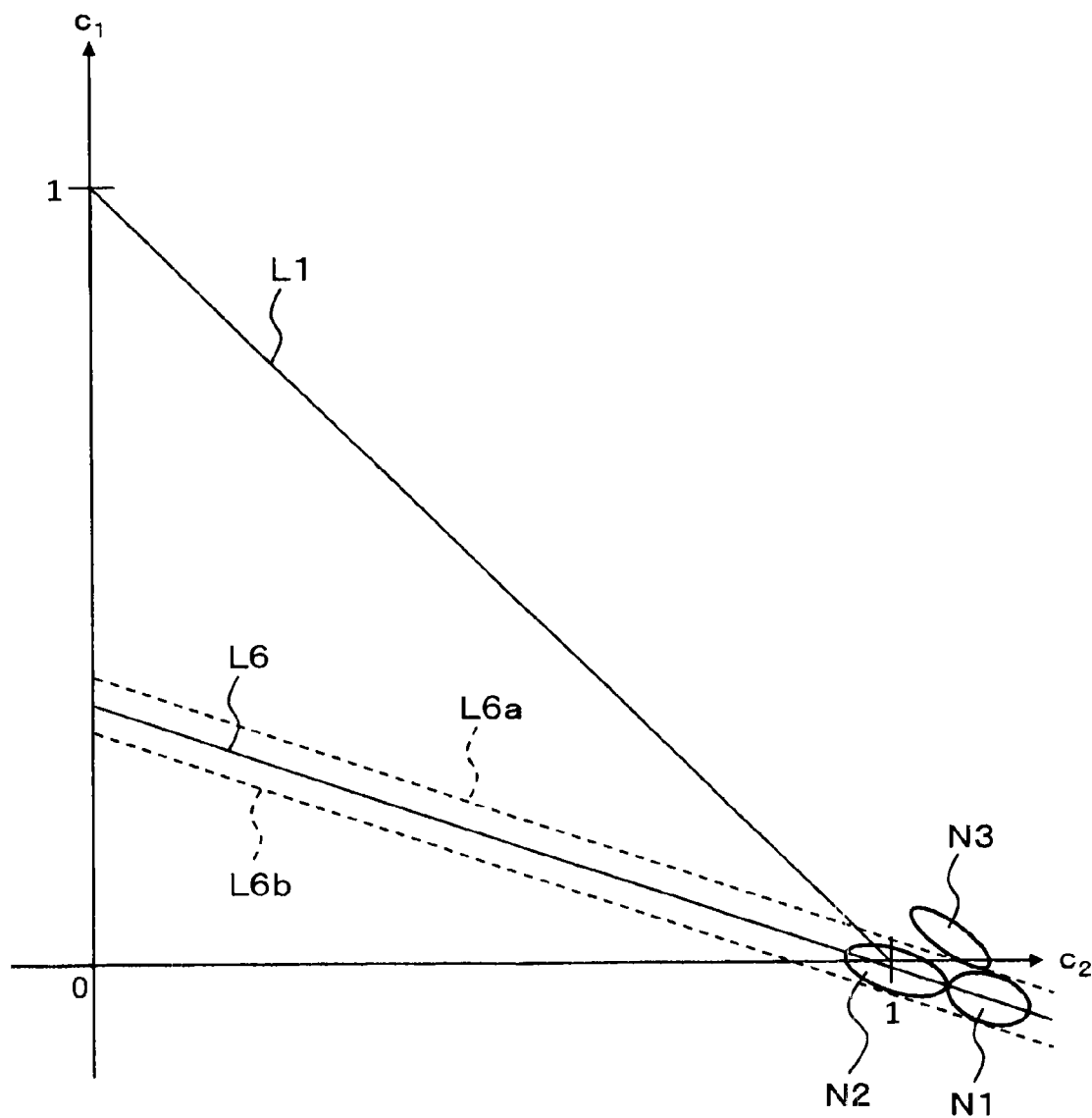
FIG. 13 is a schematic diagram for the purpose of describing the processes carried out by the X-ray CT apparatus in the third embodiment.

On the other hand, FIG. 13 shows an example of the distributions of the coordinates for uric acid, cartilage and soft tissue obtained using the method described in the first embodiment. The vertical and horizontal axes are defined based on the contrast agent and water, respectively. The distribution regions N1, N2 and N3 indicate the distributions of uric acid, cartilage and soft tissue, respectively. The straight line L6 is a straight line indicating the state of distribution of the coordinates of uric acid. Furthermore, straight lines L6a and L6b show, respectively, the upper and lower limits of the distribution range of the straight line according to the spread of the distribution region of uric acid (see the first embodiment). Illustration of the straight lines with regard to a cartilage and soft tissue are omitted; however, the directions of the straight lines can be easily ascertained from their morphologies. As can be seen from the positions of the distribution regions N1, N2 and N3, in this example, the straight lines obtained for uric acid and cartilage are close together, making distinction between the two substances difficult, while the directions of the straight lines obtained for uric acid and soft tissue are sufficiently different in order to distinguish them.

Figure 14:
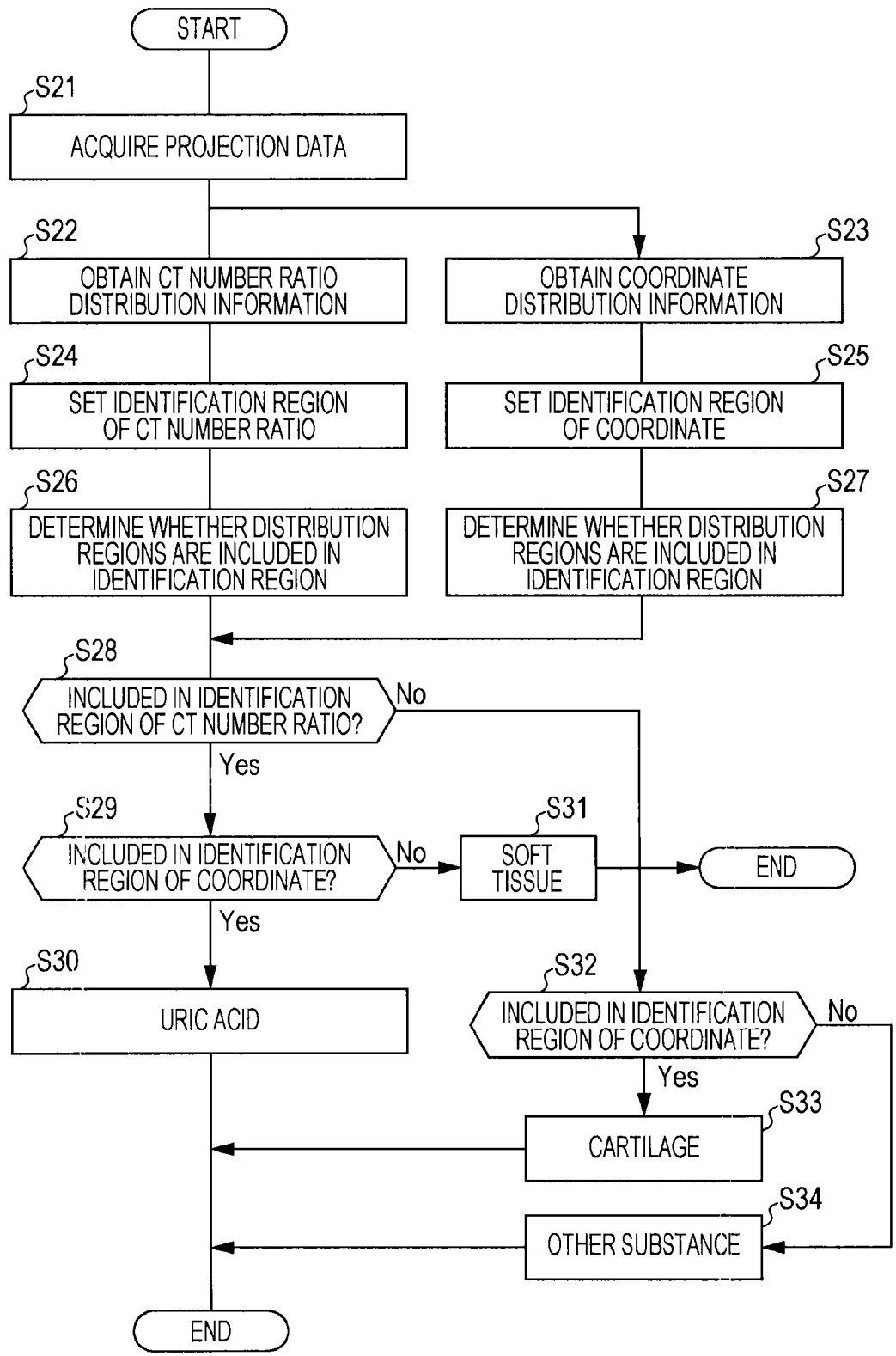
FIG. 14 is a flow chart illustrating an example of the operation of the X-ray CT apparatus in the third embodiment.

Based on the considerations above, the following is a description of an example of a process that combines the method described in the first embodiment and that described in Non-Patent Document 1 (see FIG. 14). Firstly, projection data is obtained by dual energy CT, in the same way as in the first embodiment (S21).

The reconstruction processer 3, the pixel value ratio calculator 8 and the substance identifying part 9 obtain distribution information regarding the CT number ratios shown in FIG. 12, in other words, the distribution regions K1, K2 and K3, using the same method as described above (S22). Additionally, the data processing part 4 obtains distribution information regarding the coordinates shown in FIG. 13, in other words, the distribution regions N1, N2 and N3, using the same method as described above (S23). These two pieces of distribution information are sent to the identification controller 11. Hereinafter the distribution information of the CT number ratio is referred to as the first distribution information, while the distribution information of the coordinates is referred to as the second distribution information.

The identification controller 11 identifies each of the three substances based on the first and second distribution information. As an example of this process, the identification controller 11 first obtains the straight lines M1 and M2 shown in FIG. 12, as well as the straight lines L6a and L6b shown in FIG. 13. It should be noted that the straight lines M1 and M2 and the straight lines L6a and L6b may be generated from data obtained from measurements done as part of this process, or they may be measurement data obtained in advance or regulated values (theoretical or standard values, etc.) Furthermore, the identification controller 11 may obtain, for each substance, the straight line based on the distribution region of its CT number ratio and/or the straight line based on the distribution region of its coordinate. In this way, an identification region that is sandwiched by the straight lines M1 and M2, and an identification region that is sandwiched by the straight lines L6a and L6b are obtained (S24, S25).

Subsequently, the identification controller 11 determines whether or not the distribution regions K2 or K3 of CT number ratios for each of the cartilage and soft tissue are included in the identification region that is sandwiched by the straight lines M1 and M2 (S26). This process may be: a process of determining whether or not the distribution regions K2 and K3 themselves are included in the identification region; or when a straight line is calculated in the above, a process of determining whether or not this straight line is included in the identification regions.

In the former case, it is possible to determine whether or not all of distribution regions K2 and K3 is included in the identification region, or it is possible to determine whether or not a specified proportion of the distribution regions K2 and K3 is included in the identification region.

In the latter case, depending on the length of the straight line, even though the difference in inclination is slight, the straight line may protrude from the identification region. In such a case, it is possible to set the range of the length of the straight line in advance, and to determine that the straight line is included in the identification region if the straight line is included in the identification region within the range.

Subsequently, the identification controller 11 determines whether or not the distribution regions N2 or N3 of the coordinates of each of the cartilage and soft tissue are included in the identification region that is sandwiched by the straight lines L6a and L6b (S27). This process is carried out in the same way as that for CT number ratios.

Next, the identification controller 11 distinguishes among uric acid, cartilage and soft tissue based on the result of determining whether or not the distribution regions K2 and K3 of the CT number ratios are included within the identification region, and the result of determining whether or not the distribution regions N2 and N3 of the coordinates are included in the identification region.

As a specific example of this, if it is determined that the distribution region of the CT number ratio is included within the identification region (S28: Yes), and if it is determined that the distribution region of the coordinates is included within the identification region (S29: Yes), the identification controller 11 determines that the substance corresponding to these distribution regions is uric acid (S30).

Furthermore, if it is determined that the distribution region of the CT number ratio is included within the identification region (S28: Yes), and if it is determined that the distribution region of the coordinates is not included within the identification region (S29: No), the identification controller 11 determines that the substance corresponding to these distribution regions is soft tissue (S31).

Furthermore, if it is determined that the distribution region of the CT number ratio is not included within the identification region (S28: No), and if it is determined that the distribution region of the coordinates is included within the identification region (S32: Yes), the identification controller 11 determines that the substance corresponding to these distribution regions is cartilage (S33).

Furthermore, if it is determined that the distribution region of the CT number ratio is not included within the identification region (S28: No), and if it is not determined that the distribution region of the coordinates is included within the identification region (S32: No), the identification controller 11 determines that the substance corresponding to these distribution regions is neither uric acid, cartilage nor soft tissue. This completes the explanation of this example of processing.

Next, the following is a description of the specific image forming part 10. The specific image forming part 10 forms at least one of an effective atomic number image, a density image and a monochromatic X-ray image (these are sometimes referred to as specific images). This process is implemented by combining the images expressing the distribution of the reference substances (the reference substance images) formed based on the coefficients $c_1$ and $c_2$ in the linear combination (Equation (3)) described in the first embodiment, using the method described in Patent Document 1.

An effective atomic number image is an image expressing the distribution of effective atomic numbers within the object. A density image is an image expressing the distribution of the density of substances within the object. The monochromatic X-ray image is an image that simulates the case in which the object is scanned using X-ray of a single energy level. The specific image forming part 10, which is capable of forming these images, functions as an example of the "image forming part."

The substance identifying part 43 in this embodiment is capable of identifying each of multiple target substances, based on the identification result for each of the multiple target substances obtained from the process described in the first embodiment, as well as the atomic number image, density image and/or monochromatic X-ray image formed by the specific image forming part 10 for each of the target substances. It should be noted that the process described in the first embodiment is to identify the target substance based on multiple coordinates in the coordinate system obtained in advance with regard to multiple substances, and the coordinates determined by the substance identifying part 43 with regard to the target substance.

According to the X-ray CT apparatus in this embodiment not only allows the effect obtained in the first embodiment to be obtained, but also allows the identification of substances based on both the state of distribution of coordinates for each substance in a coordinate system similar to that in the first embodiment, and the state of distribution of the CT number ratios of each substance. As a result, it is possible to identify the substances included in the object with even greater precision.

In addition, according to the X-ray CT apparatus in this embodiment allows the formation of an effective atomic number image, a density image, and/or a monochromatic X-ray image, thereby making it possible to visually ascertain the state of distribution of the substances. Furthermore, through combining substance identification process using a coordinate system, and substance identification process using these images, it is possible to identify the substances included in the object with even greater precision.

MODIFIED EXAMPLES

The following is a description of modified examples of the above embodiments.

Figure 15A:
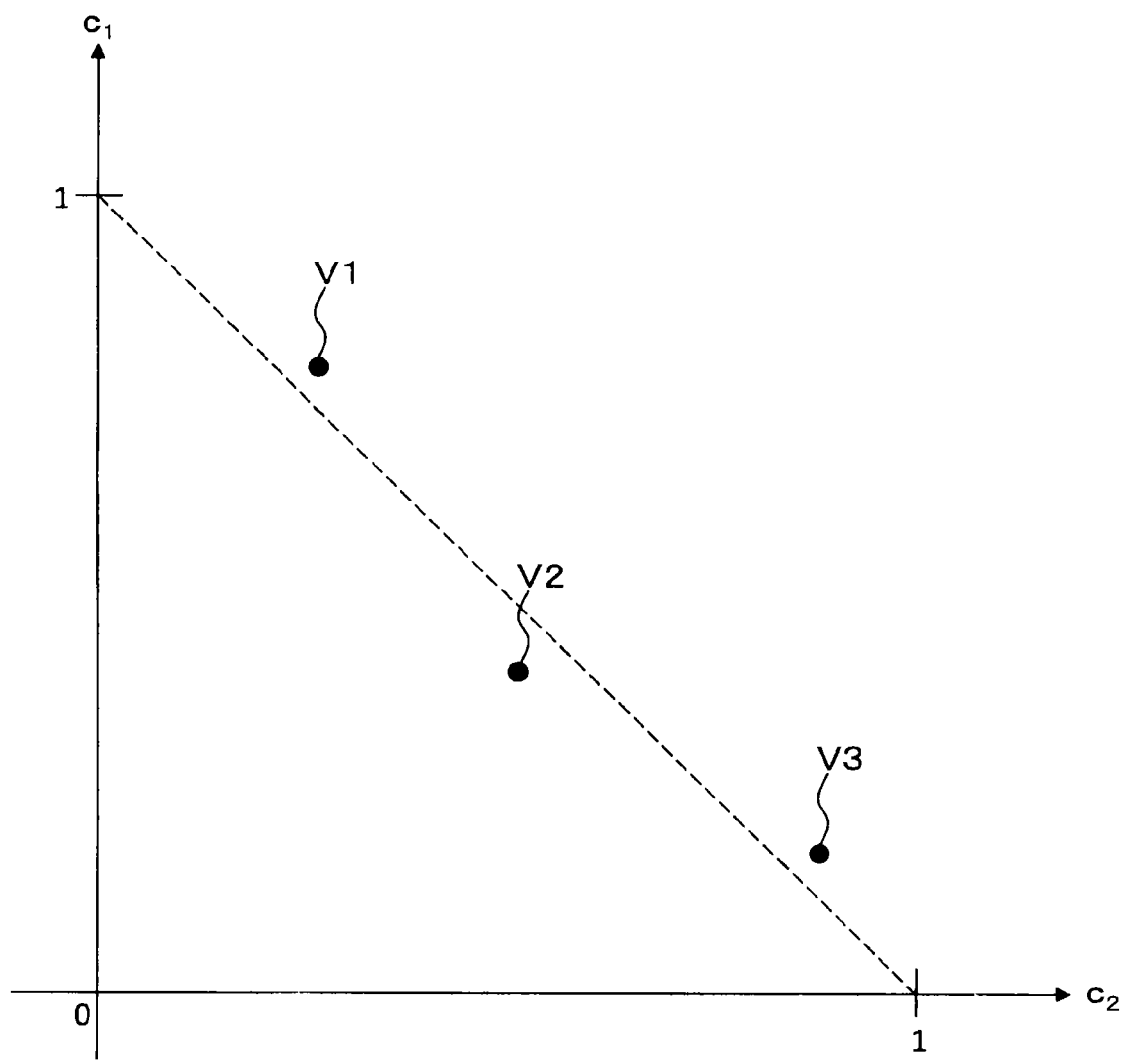
FIG. 15A is a schematic diagram for the purpose of describing a modified example of the X-ray CT apparatus.
Figure 15B:
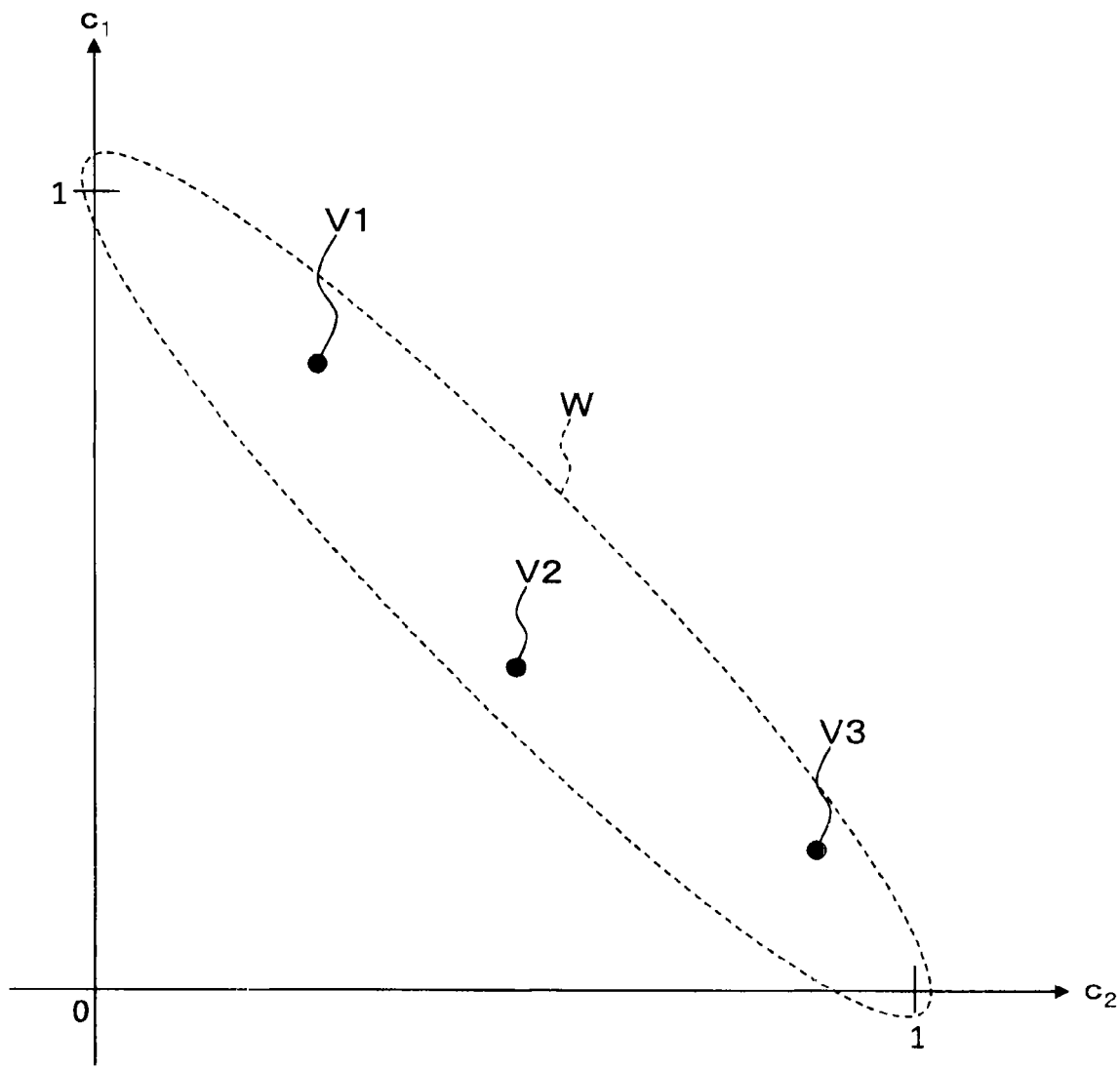
FIG. 15B is a schematic diagram for the purpose of describing a modified example of the X-ray CT apparatus.

The following is a description of the first modified example. If the target substance contains an unknown substance, it is not possible to obtain a linear correlation such as the line segment L1 shown in FIG. 5, and it is difficult to appropriately determine the region B, etc. it is assumed that, for example, as shown in FIG. 15A, three coordinates V1, V2 and V3 are obtained for three target substances. These coordinates V1, V2 and V3 are not positioned on a single straight line. In this case, this coordinate system and the coordinates V1, V2 and V3 are displayed on the display. The user refers to the displayed coordinate system and coordinates V1, V2 and V3, and arbitrarily sets a region within the coordinate system using the operation part. At this time, as shown in FIG. 15B, the region W is set such that it contains the coordinates V1, V2 and V3.

The region W is used as the distribution range for the coordinates of the density of the contrast agent, which reflects the error caused by unknown components of the object etc. For a coordinate that is not on the line segment connecting the coordinate $(c_1, c_2)=(1, 0)$ and the coordinate $(c_1, c_2)=(0, 1)$ (corresponding to the line segment L1 in FIG. 5) in the region W, a density value is associated based on this line segment. This association is carried out in the same way as the case shown in FIG. 5. The substance identifying part 43 identifies this target substance based on the positional relationship between the determined coordinate of the target substance and the region W, using, for example, the same method as that shown in the case in FIG. 5.

According to this modified example, even if an error factor such as an unknown component in the target substance intervenes, it is still possible to identify the substance with a high degree of precision, based on the judgment of the user.

The following is a description of the second modified example. The embodiments described above use the dual energy CT method which utilizes two X-rays of different energy levels; however, the embodiments are not limited to this.

For example, in an X-ray CT apparatus capable of implementing scanning using X-rays with three or more different energy levels, the generator generates N projection data by scanning the object with each of N (three or more) X-rays of different energy levels. The converter converts these N projection data into N new projection data corresponding to N reference substances. The image forming part reconstructs each of the N new projection data converted by the converter to generate N reference substance images corresponding to the N reference substances. The identifier identifies the target substance based on a correlation to the pixel values in the N reference substance images.

In the processing carried out in this case, the number of the bases of the linear combination, which is two in the embodiments above, becomes N, while the dimension of the coordinate system, which is two-dimensional in the embodiments above, becomes N-dimensional. In other words, there is no substantial difference between a case using two X-rays of different energy levels, and a case using three or more. As a result, the aforementioned embodiments can be generalized into cases using multiple (two or more) X-rays of different energy levels.

The X-ray CT apparatus in the embodiments is apparatus that displays images of the inside of an object, based on projection data obtained by scanning the object, and comprises a generator, a converter, an image forming part and an identifier. The generator generates multiple projection data by scanning the object with each of X-rays of different energy levels. The converter converts the multiple projection data into multiple new projection data corresponding to multiple reference substances. The image forming part reconstructs each of the multiple new projection data converted by the converter, thereby forming multiple reference substance images corresponding to the multiple reference substances. The identifier identifies the target substance based on a correlation of pixel values in the multiple reference substance images.

This X-ray CT apparatus facilitates the identification of substances contained within the object with a high degree of precision, similar to the embodiments above. Furthermore, the use of three or more X-rays of different energy levels allows the identification of substances with a higher degree of accuracy than the above embodiments using two X-rays.

It is also possible to similarly generalize the arbitrary configuration and processes described in the embodiments above. In this case, not only is it possible to obtain the same effects as the above embodiments, but also it is possible to achieve further improvement of the precision in identification of substances.

[Substance Identifying Method]

The substance identifying method in the embodiment is, for example, implemented by the X-ray CT apparatus in the embodiments above. The substance identifying method in the embodiment includes a generation step, a conversion step, an image forming step and an identification step. In the generation step, an object is scanned with each of X-rays of different energy levels to generate multiple projection data. In the conversion step, the multiple projection data are converted into multiple new projection data corresponding to multiple reference substances. In the image forming step, each of the multiple new projection data converted by the conversion step is reconstructed to form multiple reference substance images corresponding to multiple reference substances. In the identification step, the target substance is identified based on a correlation with pixel values in the multiple reference substance images.

The identification step may also take the form of identifying the target substance by determining whether or not corresponding pixel values within the multiple reference substance images have a predetermined correlation.

The conversion step may take the form of converting the multiple projection data into multiple new projection data corresponding to multiple reference substances using a calculation formula including the X-ray attenuation coefficient corresponding to the reference substance.

A display image generation step may be included wherein an image of the inside of the object, which is capable of distinguishing the regions of the target substances identified in the identification step.

A display image generation step may be included wherein a display image in which the pixels in the regions of the target substances identified in the identification step are either enhanced or suppressed in comparison with the pixels in other regions is generated.

A density calculation step may be included wherein density information of the target substance is calculated from corresponding pixel values in the multiple reference substance images based on a calculation formula stored in advance.

A display image generation step may be included wherein a display image representing density information is generated.

It is possible to take the form of generating multiple energy images obtained by reconstructing multiple projection data in the image forming step, and identifying the target substance based on a correlation of pixel values in the multiple reference substance images of the multiple energy images in the identification step.

It is possible to take the form of further including an image forming step in which at least one of: an effective atomic number image which represents the distribution of effective atomic numbers within the object; a density image which represents the distribution of the density of a substance within the target substance; and a monochromatic X-ray image which simulates the case in which the object is scanned using X-ray of a single energy level, and then the target substance is identified in the identification step based on the image formed by the image forming step.

According to this substance identifying method, similar to that in the first embodiment, even if substances with similar CT number ratios are considered, it is possible to distinguish them with a higher level of precision by referring to their coordinates. Additionally, it is possible to calculate the component ratio of a substance contained in the target substance, and to determine whether two or more target substances are the same kind or different kinds. Furthermore, the application of the substance identifying method in reference to the impact of noises, in the same way as the first embodiment, allows identification of substances, identification of component ratios, and separation of target substances with greater precision and accuracy.

Furthermore, according to the substance identifying method in the embodiment, similar to that in the second embodiment, in addition to the effects above, it is possible to form and display an enhanced image and/or a suppressed image. Furthermore, it is possible to visualize the density of a substance, facilitating an instinctive understanding of substance density.

Furthermore, according to the substance identifying method in the embodiment, similar to that in the third embodiment, in addition to the effects above, it is possible to aim for further improvement in accuracy of identification of a substance included in the object by identifying the substance based on both the state of distribution of coordinates of each substance and the state of distribution of CT number ratios of each substance. Additionally, since an effective atomic number image, a density image and/or a monochromatic X-ray image can be formed, it is possible to visually ascertain the state of distribution of the substance. Furthermore, by combining substance identification processing using a coordinate system and substance identification processing using these images, it is possible to aim for further improvement in accuracy of identification of a substance included in the object

[Image Processing Apparatus]

Figure 16:
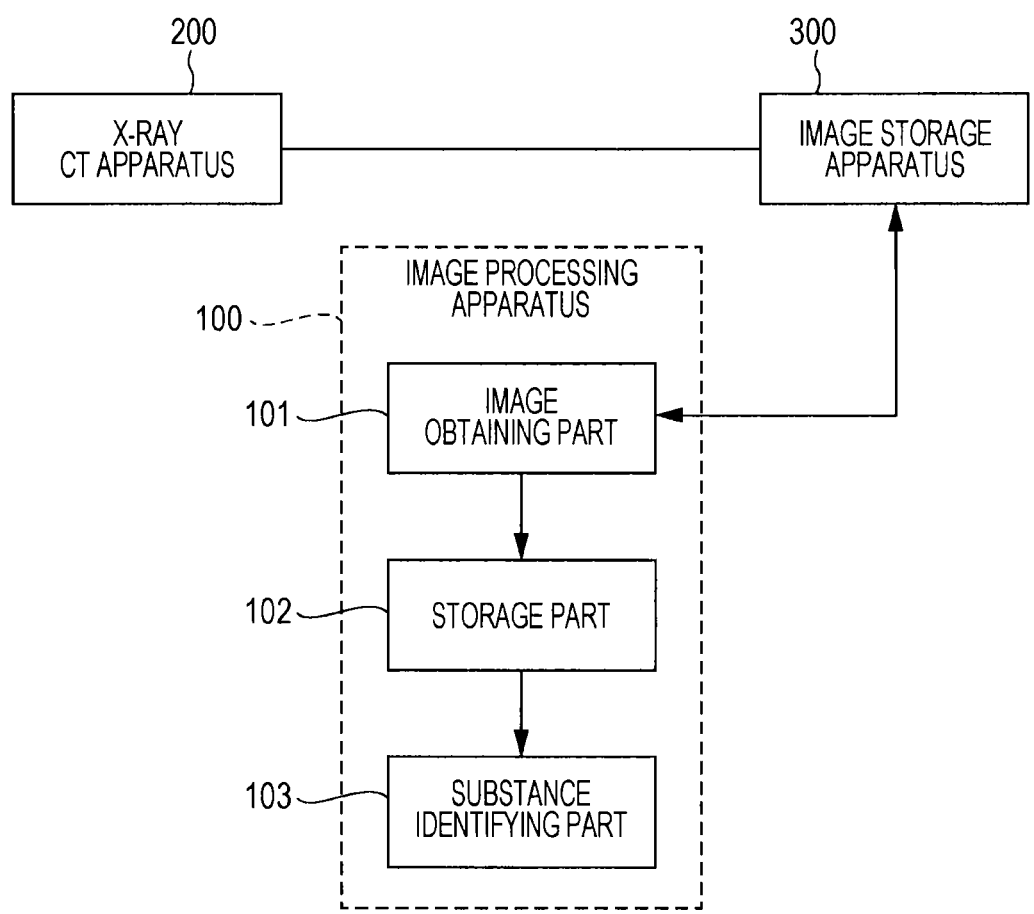
FIG. 16 is a block diagram illustrating an example of the outline of the configuration of the image processing apparatus in the embodiment.

The following is a description of the image processing apparatus in the embodiment. FIG. 16 shows the outline of the configuration of the image processing apparatus in the embodiment. An image processing apparatus 100 is connected to an image storage apparatus 300 via a network such as hospital LAN, etc. The image storage apparatus 300 stores the images formed by the X-ray CT apparatus 200.

The X-ray CT apparatus 200 may, for example, take the form of the X-ray CT apparatus in the first embodiment (see FIG. 1) with the substance identifying part 43 removed. In other words, the X-ray CT apparatus 200 is an apparatus that displays an image of the inside of the object based on projection data obtained by scanning the object, and comprises the following functions: a generation function which generates multiple projection data by scanning the object with X-rays of different energy levels; a conversion function which converts the multiple projection data into multiple new projection data corresponding to multiple reference substances; and an image forming function which reconstructs each of the multiple new projection data converted by the conversion function, thereby forming multiple reference substance images corresponding to the multiple reference substances. The X-ray CT apparatus 200 transmits the formed multiple reference substance images to the image storage apparatus 300 via a network such as the hospital LAN, etc. The image storage apparatus 300 is, for example, a PACS (Picture Archiving and Communication Systems).

The image processing apparatus 100 processes the images formed by the X-ray CT apparatus 200 and stored in the image storage apparatus 300. It should be noted that it is possible to input images into the image processing apparatus 100 by other routes. An example of such other routes is storage media in which images are stored, such as a DVD.

The image processing apparatus 100 comprises an image obtaining part 101 which obtains images from an external source. When obtaining images stored in the image storage device 300, the image obtaining part 101 comprises a communication part that communicates with the image storage device 300 via the network. Furthermore, the image obtaining part 101 may, for example, comprise: a user interface (display, operation part, etc.) for selecting images to be obtained; and a communication controller which generates a signal in order to obtain the selected images, and transmits this signal to the image storage device 300 by controlling the communication part. When obtaining images recorded in storage media, the image obtaining part 101 comprises a reading part (a driver device etc.) that is capable of reading information stored in the storage media.

The images obtained by the image obtaining part 101 are stored in a storage part 102. The storage part 102 is configured to include a storage device such as a hard disc drive. In this embodiment, the images formed using the method described above by the X-ray CT apparatus 200 are stored in the storage part 102. These images are multiple reference substance images corresponding to multiple reference substances, formed reconstructing each of multiple new projection data obtained by converting, based on multiple reference substances, multiple projection data generated by scanning the object using X-rays of different energy levels.

The substance identifying part 103 identifies the target substance based on a correlation of pixel values of the multiple reference substance images stored in the storage part 102. This process is implemented in the same way as that of the substance identifying part 43 in the first embodiment. The substance identifying part 103 functions as an example of an "identifier."

If the image processing apparatus 100 comprises a display, the result of processing by the substance identifying part 103 is displayed on the display. Furthermore, if the image processing apparatus 100 is, for example, a server on the network, the image processing apparatus 100 comprises a function (transmitter) that transmits the result of processing by the substance identifying part 103 to specified user terminals via the network. Furthermore, the image processing apparatus 100 may comprise a recording part (drive device, etc.) that records the result of processing by the substance identifying part 103 on storage media.

According to this type of image processing apparatus 100, it is possible to identify substances contained in the object with a high degree of accuracy. It should be noted that the image processing apparatus 100 may include any of the functions of the X-ray CT apparatus in the embodiments above. If any of the following configurations is applied, the operations and effects corresponding to the configuration described in the embodiments above are also applied.

For example, the substance identifying part 103 may identify the target substance by determining whether or not the pixel values corresponding to the multiple reference substance images have a preset correlation.

In addition, the image processing apparatus 100 may be provided with a display image generator, which generates images of the inside of the object, thereby making possible distinction of the regions of the target substances identified by the substance identifying part 103.

Furthermore, the image processing apparatus 100 may comprises a display image generator which generates display images wherein the pixels in the region of the target substance identified by the identifier 103 are either enhanced or suppressed in comparison with the pixels in other regions.

Additionally, the image processing apparatus 100 may be provided with a density calculator that obtains density information for the target substance from corresponding pixel values within the multiple reference substance images, based on a calculation formula that is stored in advance. In addition, the image processing apparatus 100 may be provided with a display image generator that generates display images representing density information.

Furthermore, the substance identifying part 103 may be configured to identify the target substance based on a correlation of the pixel values of the multiple reference substance images of multiple energy images.

Furthermore, the image processing apparatus 100 may be provided with a forming part which forms, based on the reference substance images, at least one of an effective atomic number image showing the distribution of effective atomic numbers within the object, a density image showing the density distribution of substances within the target substance, and a monochromatic X-ray image which simulates the case of scanning the target substance with X-rays of a single energy level, and then the substance identifying part 103 may identify the target substance based on the images formed by the forming part.

<Programs and Storage Media>

It is possible to configure programs for causing an X-ray CT apparatus or a computer included therein to implement the processes described in the above embodiments. In addition, it is possible to store programs for causing an image processing apparatus (computer) to implement the processes described in the above embodiments in storage media such as a DVD, etc. Additionally, it is possible to construct a system that transmits any of these programs via a network such as the internet or a LAN.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS

1 Gantry
2 Pre-processing part
3 Reconstruction part
4 Data processing part
41 Projection data converter
42 Image forming part
43 Substance identifying part
5 Controller
6 Display
7 Operation part
8 Pixel value ratio calculator
9 Substance identifying part
10 Specific image forming part
11 Identification controller

What is claimed is:

1. An X-ray CT apparatus that displays an image of the inside of an object based on projection data obtained by scanning the object, comprising:
    a generator that scans the object with each of X-rays of different energy levels and generates multiple projection data;
    a converter that converts the multiple projection data into multiple image data corresponding to multiple reference substances contained in the object based on a linear attenuation coefficient that varies according to the energy levels of the reference substances, and generates multiple new projection data corresponding to the reference substances according to the energy levels; and
    an identifier that identifies a target substance from an abundance ratio of each of the reference substances based on a fact that a pixel value at coordinates of each of the new projection data according to the energy levels is formed from a sum of values each obtained by multiplying the abundance ratio of each of the reference substances at the coordinates by the linear attenuation coefficient of the reference substance.

2. The X-ray CT apparatus according to claim 1, further comprising a display image generator that generates an image of the inside of the object in which the region of the target substance identified by the identifier is distinguishable.

3. The X-ray CT apparatus according to claim 1, further comprising a display image generator that generates a display image in which the pixels in the region of the target substance identified by the identifier are either enhanced or suppressed in comparison with the pixels in other regions.

4. A substance identifying method, including:
    a generation step that scans an object with each of X-rays of different energy levels and generates multiple projection data;
    a conversion step that converts the multiple projection data into multiple image data corresponding to multiple reference substances contained in the object based on a linear attenuation coefficient that varies according to the energy levels of the reference substances, and generates multiple new projection data corresponding to the reference substances according to the energy levels; and
    an identification step that identifies a target substance from an abundance ratio of each of the reference substances based on a fact that a pixel value at coordinates of each of the new projection data according to the energy levels is formed from a sum of values each obtained by multiplying the abundance ratio of each of the reference substances at the coordinates by the linear attenuation coefficient of the reference substance.

5. The substance identifying method according to claim 4, further comprising a display image generation step that generates an image of the inside of the object in which the region of the target substance identified by the identification step is distinguishable.

6. The substance identifying method according to claim 4, further comprising a display image generation step that generates a display image in which the pixels in the region of the target substance identified by the identification step are either enhanced or suppressed in comparison with the pixels in other regions.

\* \* \* \* \*